US010392426B2

(12) United States Patent
Klapoetke et al.

(10) Patent No.: US 10,392,426 B2
(45) Date of Patent: Aug. 27, 2019

(54) BLUE-LIGHT-ACTIVATED ION CHANNEL POLYPEPTIDES AND USES THEREOF

(71) Applicants: Massachusetts Institute of Technology, Cambridge, MA (US); The Governors of the University of Alberta, Edmonton (CA); President and Fellows of Harvard College, Cambridge, MA (US)

(72) Inventors: Nathan Klapoetke, Cambridge, MA (US); Edward Boyden, Chestnut Hill, MA (US); Yongku Cho, Vernon, CT (US); Brian Y. Chow, Cherry Hill, NJ (US); Gane K. S. Wong, Edmonton (CA); Adam E. Cohen, Cambridge, MA (US); Daniel R. Hochbaum, Cambridge, MA (US)

(73) Assignees: Massachusetts Institute of Technology, Cambridge, MA (US); The Governors of the University of Alberta, Edmonton, Alberta (CA); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/616,228

(22) Filed: Feb. 6, 2015

(65) Prior Publication Data

US 2015/0223679 A1    Aug. 13, 2015

Related U.S. Application Data

(60) Provisional application No. 61/937,066, filed on Feb. 7, 2014.

(51) Int. Cl.
| | |
|---|---|
| *A61B 3/00* | (2006.01) |
| *A61B 3/10* | (2006.01) |
| *A61N 5/06* | (2006.01) |
| *A61K 35/30* | (2015.01) |
| *A61K 35/34* | (2015.01) |
| *A61K 36/05* | (2006.01) |
| *A61K 38/00* | (2006.01) |
| *A61K 41/00* | (2006.01) |
| *G01N 33/50* | (2006.01) |
| *C07K 14/405* | (2006.01) |

(52) U.S. Cl.
CPC .......... *C07K 14/405* (2013.01); *A61B 3/0008* (2013.01); *A61B 3/10* (2013.01); *A61K 35/30* (2013.01); *A61K 35/34* (2013.01); *A61K 36/05* (2013.01); *A61K 41/00* (2013.01); *A61K 41/0057* (2013.01); *A61N 5/062* (2013.01); *A61N 5/0622* (2013.01); *G01N 33/5023* (2013.01); *A61K 38/00* (2013.01); *A61N 2005/0663* (2013.01)

(58) Field of Classification Search
CPC ........ A61K 36/05; A61K 35/30; A61K 35/34; A61K 41/00; A61K 38/00; A61N 5/0622; A61N 2005/0663; A61N 5/062; C07K 14/405; A61B 3/0008; A61B 3/10
See application file for complete search history.

(56) References Cited

U.S. PATENT DOCUMENTS

| | | |
|---|---|---|
| 5,041,224 A | 8/1991 | Ohyama et al. |
| 6,197,387 B1 | 3/2001 | Feidler et al. |
| 7,824,869 B2 | 11/2010 | Hegemann et al. |
| 7,939,220 B2 | 5/2011 | Oesterhelt et al. |
| 8,202,699 B2 | 6/2012 | Hegemann et al. |
| 8,401,609 B2 | 3/2013 | Deisseroth et al. |
| 2007/0053996 A1 | 3/2007 | Boyden et al. |
| 2007/0054319 A1 | 3/2007 | Boyden et al. |
| 2007/0261127 A1 | 11/2007 | Boyden et al. |
| 2009/0099038 A1 | 4/2009 | Deisseroth et al. |
| 2010/0087006 A1 | 4/2010 | Gressel et al. |
| 2010/0145418 A1 | 6/2010 | Zhang et al. |
| 2010/0234273 A1 | 9/2010 | Boyden et al. |
| 2011/0165681 A1 | 7/2011 | Boyden et al. |
| 2012/0121542 A1 | 5/2012 | Chuong et al. |
| 2012/0214188 A1 | 8/2012 | Klapoetke et al. |
| 2014/0324134 A1 | 10/2014 | Klapoetke et al. |
| 2015/0192567 A1 | 7/2015 | Chuong et al. |

FOREIGN PATENT DOCUMENTS

| | | |
|---|---|---|
| EP | 2112510 A1 | 10/2009 |
| WO | 2007024391 A3 | 3/2007 |
| WO | 2009119782 A1 | 10/2009 |
| WO | 2010056970 A2 | 5/2010 |
| WO | 2012032103 A1 | 3/2012 |
| WO | 2012061676 A1 | 5/2012 |
| WO | 2012061744 A2 | 5/2012 |
| WO | 2013071231 A1 | 5/2013 |

(Continued)

OTHER PUBLICATIONS

University of Oxford (Jan. 16, 2014). Author Unknown. http://www.ox.ac.uk/news/2014-01-16-gene-therapy-trial-shows-promise-type-blindness.*
Baliga, N.S. et al., "Genome sequence of Haloarcula marismortui: A halophilic archaeon from the Dead Sea", Genome Research, 2004, vol. 14, pp. 2221-2234.
Boyden, E. et al, "Millisecond-timescale, genetically targeted optical control of neural activity", Nature Neuroscience, Sep. 2005, vol. 8, pp. 1263-1268.
Busskamp, V. et al., "Genetic Reactivation of Cone Photoreceptors Restores Visual Responses in Retinitis Pigmentosa", Science, Jul. 23, 2010, vol. 329, pp. 413-417.
Chow, B. et al., "High-performance genetically targetable optical neural silencing by light-driven proton pumps", Nature, Jan. 7, 2010, vol. 463, pp. 98-102.

(Continued)

*Primary Examiner* — Robert S Landsman
(74) *Attorney, Agent, or Firm* — Pierce Atwood LLP

(57) ABSTRACT

The invention, in some aspects relates to light-activated ion channel polypeptides and encoding nucleic acids and also relates in part to compositions comprising light-activated ion channel polypeptides and methods using light-activated ion channel polypeptides to alter cell activity and function.

25 Claims, 5 Drawing Sheets

Specification includes a Sequence Listing.

(56) References Cited

FOREIGN PATENT DOCUMENTS

WO  2015167639 A1  11/2015

OTHER PUBLICATIONS

Chow, B. et al., "Synthetic Physiology Strategies for Adapting Tools from Nature for Genetically Targeted Control of Fast Biological Processes", Methods in Enzymology, 2011, vol. 497, pp. 425-443.
Chuong, A. et al., "Development of next-generation optical neural silencers through directed combinatorial optimization", Neuroscience 2010 Annual Meeting, Nov. 13, 2010, Presentation Abstract, 2 pages.
Chuong, A. et al., "Red-shifted optical neuronal silencing: optical hemoglobin transparency for long-distance optogenetic inhibition", Neuroscience 2010 Annual Meeting, Nov. 13, 2010, Poster Presentation, 1 page.
Dittgen, T. et al., "Lentivirus-based genetic manipulations of cortical neurons and their optical and electrophysiological monitoring in vivo", PNAS, Dec. 28, 2004, vol. 101, pp. 18206-18211.
Doroudchi, M. et al., "Virally delivered Channelrhodopsin-2 Safely and Effectively Restores Visual Function in Multiple Mouse Models of Blindness", Molecular Therapy, Jul. 2011, vol. 19, pp. 1220-1229.
Gradinaru, V. et al., "eNpHR: a Natronomonas halorhodopsin enhanced for optogenetic applications", Brain Cell Biology, 2008, vol. 36, pp. 129-139.
Gradinaru, V. et al., "Molecular and Cellular Approaches for Diversifying and Extending Optogenetics", Cell, Apr. 2, 2010, vol. 141, pp. 154-165.
Hackett, N. et al., "Structure-Function Studies on Bacteriorhodopsin", The Journal of Biological Chemistry, Jul. 5, 1987, vol. 262, pp. 9277-9284.
Han, X. & E. Boyden, "Multiple-Color Optical Activation, Silencing, and Desynchronization of Neural Activity, with Single-Spike Temporal Resolution", PLoS one, Mar. 2007, Issue 3, pp. 1-12.
Han, X. et al., "A high-light sensitivity optical neural silencer: development and application to optogenetic control of non-human primate cortex", Frontiers in Systems Neuroscience, Apr. 13, 2011, vol. 5, pp. 1-8.
Han, X. et al., "Informational lesions: optical perturbation of spike timing and neural synchrony via microbial opsin gene fusions", Frontiers in Molecular Neuroscience, Aug. 27, 2009, vol. 2, pp. 1-9.
Ihara, K. et al., "*Haloarcula argentinensis* sp. nov. and *Haloarcula mukohataei* sp. nov., Two New Extremely Halophilic Archaea Collected in Argentina", International Journal of Systematic Bacteriology, Jan. 1997, vol. 47, pp. 73-77.
Ihara, K. et al., "Evolution of the Archaeal Rhodopsins: Evolution Rate Changes by Gene Duplication and Functional Differentiation", Journal of Molecular Biology, 1999, vol. 285, pp. 163-174.
Javor, B et al., "Box-Shaped Halophilic Bacteria", Journal of Bacteriology, Sep. 1982, vol. 151, pp. 1532-1542.
Klare, J. et al., "Microbial Rhodopsins: Scaffolds for Ion Pumps, Channels, and Sensors", Results and Problems in Cell Differentiation Journal Impact Factor & Information, Sep. 27, 2007, vol. 45, pp. 73-122.
Kitajima, T. et al. "Novel Bacterial Rhodopsins from Haloarcula vallismortis", Biochemical and Biophysical Research Communications,1996, vol. 220, pp. 341-345.
Kleinlogel, S. et al., "Ultra-light sensitive and fast neuronal activation with the Ca(2+)-permeable channelrhodopsin CatCh", Nature Neuroscience, Apr. 2011, vol. 14, pp. 513-518.
Lin, J. et al., "Characterization of Engineered Channelrhodopsin Variants with Improved Properties and Kinetics", Biophysical Journal, Mar. 4, 2009, vol. 96, pp. 1803-1814.
Mogi, T. et al, "Structure-Function Studies on Bacteriorhodopsin", The Journal of Biological Chemistry, Aug. 25, 1989, vol. 264, pp. 14197-14201.
Nagel, G. et al., "Channelrhodopsin-1: A Light-Gated Proton Channel in Green Algae", Science, Jun. 28, 2002, vol. 296, pp. 2395-2398.
Nagel, G. et al., "Channelrhodopsin-2, a directly light-gated cation-selective membrane channel", PNAS, Nov. 25, 2003, vol. 100, pp. 13940-13945.
Otomo, J., "Anion selectivity and pumping mechanism of halorhodopsin", Biophysical Chemistry, 1995, vol. 56, pp. 137-141.
Otomo, J. et al. "Bacterial rhodopsins of newly isolated halobacteria", Journal of General Microbiology, Jan. 6, 1992, vol. 138, pp. 1027-1037.
Otomo, J. & T. Muramatsu, "Over-expression of a new photo-active halorhodopsin in Halobacterium salinarium", Biochimica et Biophysica Acta, Aug. 1995, vol. 1240, pp. 248-256.
Rudiger, M. & D. Oesterhelt, "Specific arginine and threonine residues control anion binding and transport in the light-driven chloride pumo halorhodopsin", The EMBO Journal, 1997, vol. 16, pp. 3813-3821.
Tang et al., "Faithful Expression of Multiple Proteins via 2A-Peptide Self-Processing: A Versatile and Reliable Method for Manipulating Brain Circuits", The Journal of Neuroscience, Jul. 8, 2009, vol. 29, pp. 8621-8629.
Wang, H. et al., "High-speed mapping of synaptic connectivity using photostimulation in Channelrhodopsin-2 transgenic mice", PNAS, May 8, 2007, vol. 104, pp. 8143-8148. Epub May 1, 2007.
Yizhar, O. et al., "Neocortical excitation/inhibition balance in information processing and social dysfunction", Nature, Sep. 8, 2011, vol. 477, pp. 1-8.
Zhang, F. et al., "Multimodal fast optical interrogation of neural circuitry" Nature, 2007, pp. 633-639, vol. 446.
Zhang, F. et al., "Red-shifted optogenetic excitation: a tool for fast neural control derived from Volvox carteri", Nature Neuroscience, 2008, vol. 11, pp. 631-633.
Atasoy, D. et al., "A Flex switch targets Channelrhodopsin-2 to multiple cell types for imaging and long-range circuit mapping", Journal of Neuroscience, Jul. 9, 2008, vol. 28, pp. 7025-7030.
Campagnola, L. et al., "Fiber-coupled light-emitting diode for localized photostimulation of neurons expressing channelrhodopsin-2", Journal of Neuroscience Methods, Mar. 30, 2008, vol. 169, pp. 27-33.
Feldbauera, K. et al., "Channelrhodopsin-2 is a leaky proton pump", PNAS, Jul. 28, 2009, vol. 106, pp. 12317-12322.
Kuhlman, S. and Z. J. Huang, "High-Resolution Labeling and Functional Manipulation of Specific Neuron Types in Mouse Brain by Cre-Activated Viral Gene Expression", PLoS One, Apr. 2008, vol. 3, pp. 1-11.
Mukohata, Y. et al., "Halobacterial Rhodopsins", Journal of Biochemistry, 1999, vol. 125, pp. 649-657.
Munoz-Jordan, J. et al., "Inhibition of Alpha/Beta Interferon Signaling by the NS4B Protein of Flaviviruses", Journal of Virology, Jul. 2005, vol. 79, pp. 8004-8013.
Sena-Esteves, M. et al., "Optimized large-scale production of high titer lentivirus vector pseudotypes", Journal of Virological Methods, Dec. 15, 2004, vol. 122, pp. 131-139.
International Search Report and Written Opinion dated Oct. 7, 2015 for International Patent Application No. PCT/2015/014886, 13 pages.
Klapoetke, N. et al., "Independent optical excitation of distinct neural populations", Nature Methods, Mar. 2014, vol. 11, pp. 338-346.
"UPI0003E33891", Jan. 31, 2014, Retrieved from the Internet: URL:http://www.uniprot.org/uniparc/UPI0003E33891[copy retrieved on Dec. 4, 2015].
"XP55215975", Jan. 30, 2014, Retrieved from the Internet: URL:http://www.ebi.ac.uk/ena/data/view/AHH02107&display=text, [retrieved on Sep. 24, 2015].
International Preliminary Report on Patentability and Written Opinion received for PCT Patent Application No. PCT/US2015/014886, dated Aug. 18, 2016, 8 pages.
Radu, I., et al., "Conformational changes of channelrhodopsin-2", J Am Chem Soc., Jun. 3, 2009, vol. 131, 1 page. Abstract only.

(56) References Cited

OTHER PUBLICATIONS

Sugiyama, Y., et al., "Photocurrent attenuation by a single polar-to-nonpolar point mutation of channelrhodopsin-2", Photochem Photobiol Sci., Mar. 2009, vol. 8, 1 page. Abstract only.
Nack, M., "The DC gate in Channelrhodopsin-2: crucial hydrogen bonding interaction between C128 and D156", Photochem Photobiol Sci., Feb. 2010, vol. 9, 1 page. Abstract only.
Bi, Anding, et al., "Ectopic Expression of a Microbial-Type Rhodopsin Restores Visual Responses in Mice with Photoreceptor Degeneration", PMC, Jul. 6, 2006, 20 pages.
Krook-Magnuson, Ester, et al., "On-demand optogenetic control of spontaneous seizures in temporal lobe epilipsy", Nature Communications, Jan. 22, 2013, 8 pages.

* cited by examiner

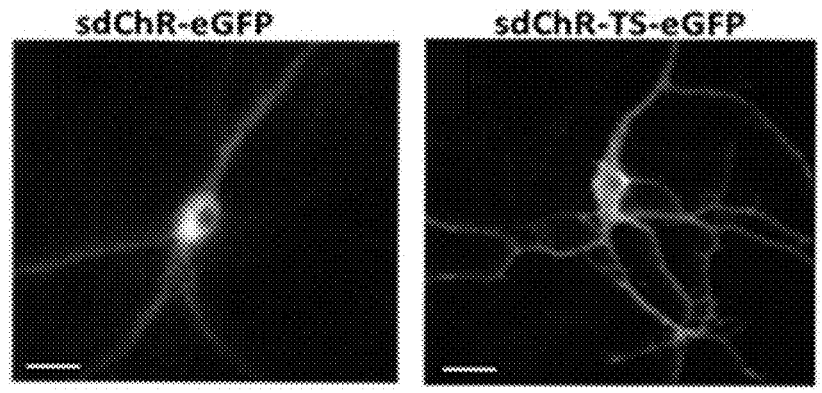
Fig. 3A  Fig. 3B
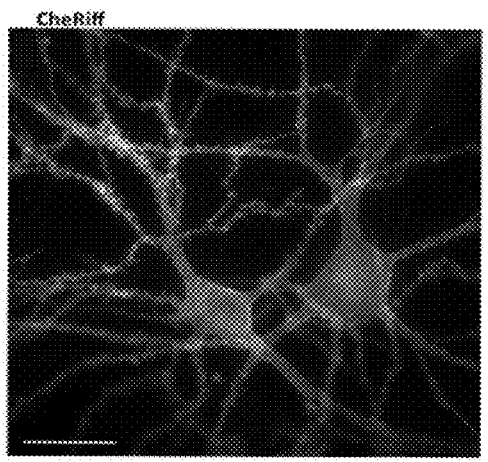
Fig. 3C
| Mutant | Trafficking | Blue photocurrent (pA; peak, 0.5 W/cm²) | Red photocurrent (pA; 640 nm, 300 W/cm²) | $t_{off}$ (ms) |
|---|---|---|---|---|
| sdChR-eGFP | ✗ | | | |
| sdChR-TS-eGFP | ✓ | 2470±170 ✓ | 38±4 ✗ | 26±2.9 ✗ |
| CheRiff (sdChR-E154A-TS-eGFP) | ✓ | 2030±100 ✓ | 10.5±2.8 ✓ | 16±0.5 ✓ |
Fig. 3D

 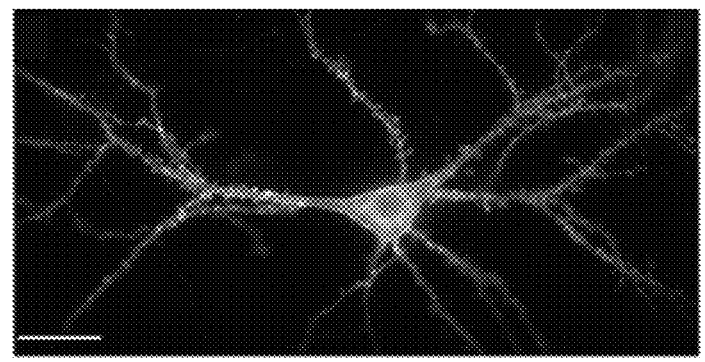
Fig. 5AFig. 5B
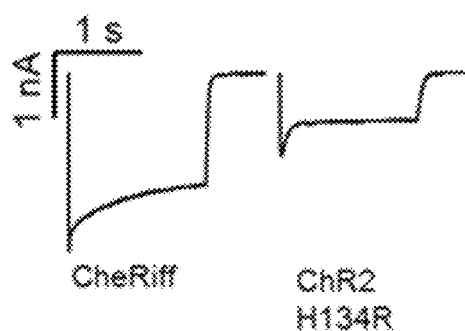
Fig. 5C
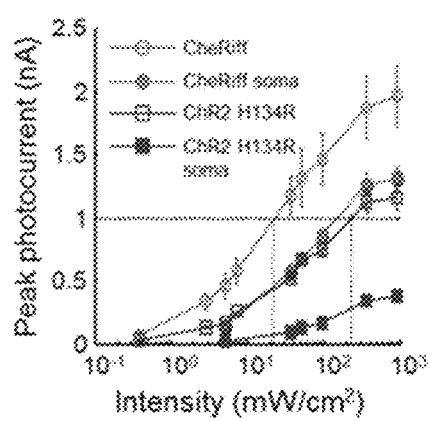 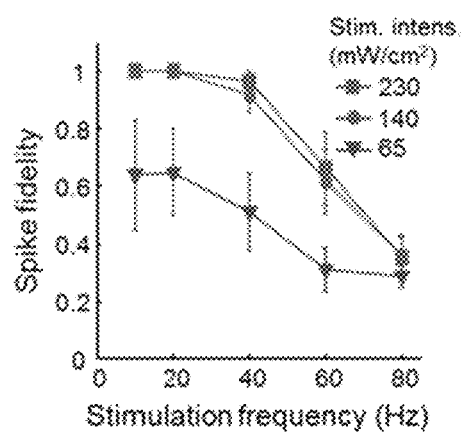
Fig. 5DFig. 5E

US 10,392,426 B2

SEQUENCE LISTING

```
<160> NUMBER OF SEQ ID NOS: 12

<210> SEQ ID NO 1
<211> LENGTH: 948
<212> TYPE: DNA
<213> ORGANISM: Artificial Sequence
<220> FEATURE:
<223> OTHER INFORMATION: Synthetic Oligonucleotide, Mammalian-condon
      optimized DNA

<400> SEQUENCE: 1
atgggcggag ctcctgctcc agacgctcac agcgcccac  ctggaaacga ttctgccgga      60
ggcagtgagt accatgcccc agctggatat caagtgaatc caccctacca ccccgtgcat     120
gggtatgagg aacagtgcag ctccatctac atctactatg gggccctgtg ggagcaggaa    180
acagctaggg gcttccagtg gtttgccgtg ttcctgtctg ccctgtttct ggctttctac    240
ggctggcacg cctataaggc cagcgtggga tgggaggaag tgtacgtgtg ctccgtggag    300
ctgatcaaag tgattctgga gatctatttc gagttcacca gtcctgctat gctgttcctg    360
tacggaggga acattacccc atggctgaga tatgccgaat ggctgctgac atgtcccgtg    420
atcctgattc atctgtctaa catcaccggc ctgagtgagg aatacaataa gcggacaatg    480
gctctgctgg tgtccgacct gggaactatt tgcatggag  tgacagccgc tctggccact    540
gggtgggtga agtggctgtt ttactgtatc ggcctggtgt atggaaccca gacattctac    600 aacgctgaa  tcatctacgt ggagtcttac tatatcatgc ctgccggcgg ctgtaagaaa    660
ctggtgctgg ccatgactgc cgtgtactat tctagttggc tgatgtttcc cggcctgttc    720
```

```
atctttgggc ctgaaggcat gcacaccctg agcgtggctg ggtccactat tggccatacc    780
atcgccgacc tgctgtccaa gaatatttgg ggactgctgg ggcacttcct gcggatcaaa    840
attcacgagc atatcattat gtacggcgat atcaggagac cagtgagctc ccagtttctg    900
ggacgcaagg tggacgtgct ggccttcgtg acagaggaag ataaagtg                 948
```

<210> SEQ ID NO 2
<211> LENGTH: 316
<212> TYPE: PRT
<213> ORGANISM: Scherffelia dubia

<400> SEQUENCE: 2

```
Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Glu Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
    130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
    290                 295                 300

Asp Val Leu Ala Phe Val Thr Glu Glu Asp Lys Val
305                 310                 315
```

<210> SEQ ID NO 3

<211> LENGTH: 864
<212> TYPE: DNA
<213> ORGANISM: Artificial Sequence
<220> FEATURE:
<223> OTHER INFORMATION: Synthetic Oligonucleotide, Mammalian-condon
    optimized DNA

<400> SEQUENCE: 3

| | | | | | |
|---|---|---|---|---|---|
| atgctgggaa | acggcagcgc | cattgtgcct | atcgaccagt | gcttttgcct | ggcttggacc | 60 |
| gacagcctgg | aaagcgatac | agagcagctg | gtggccaaca | tcctccagtg | gttcgccttc | 120 |
| ggcttcagca | tcctgatcct | gatgttctac | gcctaccaga | cttggagagc | cacttgcggt | 180 |
| tgggaggagg | tctacgtctg | ttgcgtcgag | ctgaccaagg | tcatcatcga | gttcttccac | 240 |
| gagttcgacg | accccagcat | gctgtacctg | gctaacggac | accgagtcca | gtggctgaga | 300 |
| tacgcagagt | ggctgctgac | ttgtcccgtc | atcctgatcc | acctgagcaa | cctgaccggc | 360 |
| ctgaaggacg | actacagcaa | gcggaccatg | aggctgctgg | tgtcagacgt | gggaaccatc | 420 |
| gtgtggggag | ctacaagcgc | catgagcaca | ggctacgtca | aggtcatctt | cttcgtgctg | 480 |
| ggttgcatct | acggcgccaa | caccttcttc | cacgccgcca | aggtgtatat | cgagagctac | 540 |
| cacgtggtgc | aaagggcag | acctagaacc | gtcgtgcgga | tcatggcttg | gctgttcttc | 600 |
| ctgtcttggg | gcatgttccc | cgtgctgttc | gtcgtgggac | agaaggatt | cgacgccatc | 660 |
| agcgtgtacg | gctctaccat | ggccacacc | atcatcgacc | tcatgagcaa | gaattgttgg | 720 |
| ggcctgctgg | acactatct | gagagtgctg | atccaccagc | acatcatcat | ctacggcgac | 780 |
| atccggaaga | gaccaagat | caacgtggcc | ggcgaggaga | tggaagtgga | gaccatggtg | 840 |
| gaccaggagg | acgaggagac | agtg | | | | 864 |

<210> SEQ ID NO 4
<211> LENGTH: 288
<212> TYPE: PRT
<213> ORGANISM: Chloromonas oogama

<400> SEQUENCE: 4

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Thr Val
        275                 280                 285

<210> SEQ ID NO 5
<211> LENGTH: 927
<212> TYPE: DNA
<213> ORGANISM: Artificial Sequence
<220> FEATURE:
<223> OTHER INFORMATION: Synthetic Oligonucleotide, mammalian-codon
      optimized DNA

<400> SEQUENCE: 5
atggactatg gcggcgcttt gtctgccgtc ggacgcgaac ttttgttcgt tactaatcct      60
gtggtggtga acgggtccgt cctggtccct gaggatcaat gttactgtgc cggatggatt     120
gaatctcgcg gcacgaacgg cgctcagacc gcgtcaaatg tcctgcagtg gcttgcagca     180
ggattcagca ttttgctgct gatgttctat gcctaccaaa cctggaaatc tacatgcggc     240
tgggaggaga tctatgtgtg cgccattgaa atggttaagg tgattctcga gttctttttt     300
gagtttaaga tccctctat gctctacctt gccacaggac accgggtgca gtggctgcgc     360
tatgcagagt ggctgctcac ttgtcctgtc atccttatcc acctgagcaa cctcaccggc     420
ctgagcaacg actacagcag gagaaccatg ggactccttg tctcagacat cgggactatc     480
gtgtggggg ctaccagcgc catggcaacc ggctatgtta agtcatctt cttttgtctt     540
ggattgtgct atggcgcgaa acattttttt cacgccgcca agcatatat cgagggttat     600
catactgtgc caaagggtcg gtgccgccag gtcgtgaccg gcatggcatg gctgttttc     660
gtgagctggg gtatgttccc aattctcttc attttgggc ccgaaggttt tggcgtcctg     720
agcgtctatg gctccaccgt aggtcacacg attattgatc tgatgagtaa aaattgttgg     780
gggttgttgg gacactacct gcgcgtcctg atccacgagc acatattgat tcacggagat     840
atccgcaaaa ccaccaaact gaacatcggc ggaacggaga tcgaggtcga gactctcgtc     900
gaagacgaag ccgaggccgg agccgtg                                         927

<210> SEQ ID NO 6
<211> LENGTH: 309
<212> TYPE: PRT
<213> ORGANISM: Chlamydomonas reinhardtii

<400> SEQUENCE: 6

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

```
Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 7
<211> LENGTH: 316
<212> TYPE: PRT
<213> ORGANISM: Artificial Sequence
<220> FEATURE:
<223> OTHER INFORMATION: Synthetic polypeptide

<400> SEQUENCE: 7

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
            35                  40                  45

Ile Tyr Ile Tyr Tyr Gly Ala Leu Trp Glu Gln Glu Thr Ala Arg Gly
        50                  55                  60

Phe Gln Trp Phe Ala Val Phe Leu Ser Ala Leu Phe Leu Ala Phe Tyr
65                  70                  75                  80
```

```
Gly Trp His Ala Tyr Lys Ala Ser Val Gly Trp Glu Glu Val Tyr Val
                 85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
            115                 120                 125

Leu Arg Tyr Ala Glu Trp Leu Leu Thr Cys Pro Val Ile Leu Ile His
        130                 135                 140

Leu Ser Asn Ile Thr Gly Leu Ser Glu Ala Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
            195                 200                 205

Ser Tyr Tyr Ile Met Pro Ala Gly Gly Cys Lys Lys Leu Val Leu Ala
        210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
        290                 295                 300

Asp Val Leu Ala Phe Val Thr Glu Glu Asp Lys Val
305                 310                 315

<210> SEQ ID NO 8
<211> LENGTH: 288
<212> TYPE: PRT
<213> ORGANISM: Artificial Sequence
<220> FEATURE:
<223> OTHER INFORMATION: Synthetic polypeptide

<400> SEQUENCE: 8

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
                20                  25                  30

Asn Ile Leu Gln Trp Phe Ala Phe Gly Phe Ser Ile Leu Ile Leu Met
            35                  40                  45

Phe Tyr Ala Tyr Gln Thr Trp Arg Ala Thr Cys Gly Trp Glu Glu Val
        50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Ala Tyr Ser Lys Arg
        115                 120                 125
```

```
Thr Met Arg Leu Leu Val Ser Asp Val Gly Thr Ile Val Trp Gly Ala
        130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
ttctgctacg agaatgaagt g                                          21

<210> SEQ ID NO 10
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 10

Phe Cys Tyr Glu Asn Glu Val
1               5

<210> SEQ ID NO 11
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 11
aaatccagaa ttacttctga agggagtat atccctctgg atcaaataga catcaatgt    59

<210> SEQ ID NO 12
<211> LENGTH: 20
<212> TYPE: PRT
<213> ORGANISM: Artificial Sequence
<220> FEATURE:
<223> OTHER INFORMATION: Synthetic polypeptide
```

```
<400> SEQUENCE: 12

Lys Ser Arg Ile Thr Ser Glu Gly Glu Tyr Ile Pro Leu Asp Gln Ile
1               5                   10                  15

Asp Ile Asn Val
            20
```

BLUE-LIGHT-ACTIVATED ION CHANNEL POLYPEPTIDES AND USES THEREOF

RELATED APPLICATIONS

This application claims benefit under 35 U.S.C. § 119(e) of U.S. Provisional application Ser. No. 61/937,066 filed Feb. 7, 2014, the disclosure of which is incorporated by reference herein in its entirety.

GOVERNMENT INTEREST

This invention was made with government support under NSF CBET 1053233 awarded by the National Science Foundation; NIH 1R01DA029639 and NIH 1R01NS075421 both awarded by the National Institutes of Health; and DARPA HR0011-12-C-0068, awarded by the Department of Defense. The government has certain rights in the invention.

FIELD OF THE INVENTION

The invention, in some aspects relates to compositions and methods for altering cell activity and function and the use of light-activated ion channels.

BACKGROUND OF THE INVENTION

Altering and controlling cell membrane and subcellular region ion permeability has permitted examination of characteristics of cells, tissues, and organisms. Light-driven pumps and channels have been used to silence or enhance cell activity and their use has been proposed for drug screening, therapeutic applications, and for exploring cellular and subcellular function.

Molecular-genetic methods for preparing cells that can be activated (e.g., depolarized) or inactivated (e.g., hyperpolarized) by specific wavelengths of light have been developed (see, for example, Han, X. and E. S. Boyden, 2007, PLoS ONE 2, e299). It has been identified that the light-activated cation channel channelrhodopsin-2 (ChR2), and the light-activated chloride pump halorhodopsin (Halo/NpHR), when transgenically expressed in cell such as neurons, make them sensitive to being activated by blue light, and silenced by yellow light, respectively (Han, X. and E. S. Boyden, 2007, PLoS ONE 2(3): e299; Boyden, E. S., et. al., 2005, Nat Neurosci. 2005 Sep.; 8(9):1263-8. Epub 2005 Aug. 14.). Previously identified light-activated pumps and channels have been restricted to activation by particular wavelengths of light, thus limiting their usefulness.

SUMMARY OF THE INVENTION

The invention, in part, relates to isolated light-activated ion channel polypeptides and methods for their preparation and use. The invention also includes isolated nucleic acid sequences that encode light-driven ion channels of the invention as well as vectors and constructs that comprise such nucleic acid sequences. In addition, the invention in some aspects includes expression of light-activated ion channel polypeptides in cells, tissues, and organisms as well as methods for using the light-activated ion channels to alter cell and tissue function and for use in diagnosis and treatment of disorders.

The invention, in part, also relates to methods for adjusting the voltage potential of cells, subcellular regions, or extracellular regions. Some aspects of the invention include methods of incorporating at least one nucleic acid sequence encoding a light-driven ion channel into at least one target cell, subcellular region, or extracellular region, the ion channel functioning to change transmembrane passage of ions in response to a specific wavelength of light. Exposing an excitable cell that includes an expressed light-driven ion channel of the invention to a wavelength of light that activates the channel, may result in depolarization of the excitable cell. By contacting a cell that includes a light-activated ion channel polypeptide of the invention with particular wavelengths of light, the cell is depolarized. A plurality of light-activated ion channels activated by different wavelengths of light may be used to achieve multi-color depolarization.

In some embodiments, the invention comprises a method for the expression of certain classes of genes encoding for light-driven ion channels, in genetically-targeted cells, to allow millisecond-timescale generation of depolarizing current in response to pulses of light. These channels can be genetically-expressed in specific cells (e.g., using a virus) and then used to control cells in intact organisms (including humans) as well as cells in vitro, in response to pulses of light. Given that these channels have different activation spectra from one another and from the prior channels (e.g., ChR2/VChR1), they also allow multiple colors of light to be used to depolarize different sets of cells in the same tissue, simply by expressing channels with different activation spectra genetically in different cells, and then illuminating the tissue with different colors of light.

In some aspects, the invention uses eukaryotic channelrhodopsins, such as *Scherffelia dubia* and *Chloromonas oogama* rhodopsin to depolarize excitable cells. These channelrhodopsins can also be used to modify the pH of cells, or to introduce cations as chemical transmitters.

The ability to optically perturb, modify, or control cellular function offers many advantages over physical manipulation mechanisms, such as speed, non-invasiveness, and the ability to easily span vast spatial scales from the nanoscale to macroscale. One such approach is an opto-genetic approach, in which heterologously expressed light-activated membrane polypeptides such as a light-activated ion channel polypeptide of the invention, are used to move ions with various spectra of light.

According to one aspect of the invention, isolated light-activated ion channel polypeptides are provided. The isolated light-activated ion channel polypeptides, when expressed in a membrane and contacted with blue light are activated, and wherein the polypeptide comprises a wild-type or modified *Scherffelia* or *Chloromonas* channelrhodopsin polypeptide sequence. In some embodiments, the *Scherffelia* polypeptide sequence is a *Scherffelia dubia* polypeptide sequence and the *Chloromonas* polypeptide sequence is a *Chloromonas oogama* polypeptide sequence. In certain embodiments, contacting the expressed ion channel with red light does not activate the ion channel. In some embodiments, the activating blue light has a wavelength in a range from about 450 nm to about 495 nm. In some embodiments, the red light has a wavelength of about 620 nm to about 690 nm. In some embodiments, the polypeptide comprises the amino acid sequence of ChR64 (SEQ ID NO:2) or ChR86 (SEQ ID NO:4). In certain embodiments, the modified *Scherffelia* channelrhodopsin polypeptide sequence comprises an E→A substitution at an amino acid residue corresponding to amino acid 154 of the amino acid sequence of ChR64 (SEQ ID NO:2). In some embodiments, the modified *Scherffelia* channelrhodopsin polypeptide sequence is the sequence set forth as SEQ ID NO:7. In some embodiments, the modified *Chloromonas* channelrhodopsin polypeptide sequence comprises a D→A substitution at an amino acid residue corresponding to amino acid 124 of the amino acid sequence of ChR86 (SEQ ID NO:4). In certain embodiments, the modified *Chloromonas* channelrhodopsin polypeptide sequence is the sequence set forth as SEQ ID NO:8.

According to another aspect of the invention, a cell that includes of any of the aforementioned embodiments of isolated light-activated ion channel polypeptides is provided. In some embodiments, the light-activated ion channel is activated and the cell depolarized when the light-activated ion channel is contacted with light under suitable conditions for depolarization of the cell. In some embodiments, the cell is an excitable cell. In some embodiments, the cell is a mammalian cell. In certain embodiments, the cell is in vitro, ex vivo, or in vivo. In some embodiments, the cell also includes one, two, three, four, or more additional light-activated ion channel polypeptides, wherein at least one, two, three, four, or more of the additional light-activated ion channel polypeptides is activated by contact with light having a non-blue light wavelength.

According to another aspect of the invention, an isolated nucleic acid sequence that encodes any one of the aforementioned isolated light-activated ion channel polypeptides is provided. In certain embodiments, the sequence comprises the sequence set forth as SEQ ID NO:1, or SEQ ID NO:3. In some embodiments, the nucleic acid sequence is a mammalian codon-optimized DNA sequence. In some embodiments, the light-activated ion pump encoded by the nucleic acid sequence is expressed in the cell.

According to another aspect of the invention, a vector that includes any of the aforementioned embodiments of an isolated nucleic acid is provided. In some embodiments, the vector also comprises a trafficking sequence. In some embodiments, the nucleic acid sequence is operatively linked to a promoter sequence. In certain embodiments, the vector also includes one, two, or more nucleic acid signal sequences operatively linked to the nucleic acid sequence encoding the light-activated ion channel. In some embodiments, the vector is a plasmid vector, cosmid vector, viral vector, or an artificial chromosome.

According to another aspect of the invention, a cell that includes any aforementioned embodiment of a vector is provided. In certain embodiments, the cell also includes one, two, three, four, or more additional light-activated ion channels, wherein at least one, two, three, four, or more of the additional light-activated ion channels is activated by contact with light having a non-blue light wavelength.

According to another aspect of the invention, methods of depolarizing a cell are provided. The methods include contacting a cell that includes any aforementioned embodiment of an isolated light-activated ion channel polypeptide, with a blue light under conditions suitable to depolarize the cell and depolarizing the cell. In some embodiments, the light-activated ion channel activates in response to blue light in a range from about 450 nm to about 495 nm. In some embodiments, the light-activated ion channel polypeptide is encoded by the nucleic acid sequence set forth as SEQ ID NO:1 or SEQ ID NO:3. In certain embodiments the amino acid sequence of the light-activated ion channel polypeptide sequence includes the sequence set forth as SEQ ID NO:2, SEQ ID NO:4, SEQ ID NO:7, or SEQ ID NO:8. In some embodiments the light-activated ion channel is not activated in response to contact with red light. In some embodiments, the cell is a nervous system cell, a cardiac cell, a circulatory system cell, a visual system cell, an auditory system cell, or a muscle cell. In certain embodiments, the cell is a mammalian cell. In some embodiments, the cell additionally includes one, two, three, or more additional light-activated ion channel polypeptides, wherein at least one, two, three, four, or more of the additional light-activated ion channel polypeptides is activated by contact with light having a non-blue light wavelength and is not activated by light having a blue light wavelength in a range from about 450 nm to about 495 nm. In some embodiments, the cell is in a subject and depolarizing the cell diagnoses or assists in a diagnosis of a disorder in the subject. In some embodiments, the cell is in a subject and depolarizing the cell treats a disorder in the subject.

According to yet another aspect of the invention, methods of assessing the effect of a candidate compound on a cell are provided. The methods include a) contacting a test cell that includes any aforementioned embodiment of an isolated light-activated ion channel with blue light under conditions suitable for depolarization of the cell; b) contacting the test cell with a candidate compound; and c) identifying the presence or absence of a change in depolarization or a change in a depolarization-mediated cell characteristic in the test cell contacted with the blue light and the candidate compound compared to depolarization or a depolarization-mediated cell characteristic, respectively, in a control cell contacted with the blue light and not contacted with the candidate compound; wherein a change in depolarization or a depolarization-mediated cell characteristic in the test cell compared to the control indicates an effect of the candidate compound on the test cell. In certain embodiments, the blue light has a wavelength in a range from about 450 nm to about 495 nm. In some embodiments, the effect of the candidate compound is an effect on the depolarization of the test cell. In some embodiments, the effect of the candidate compound is an effect on a depolarization-mediated cell characteristic in the test cell. In certain embodiments, the method further includes characterizing the change identified in the depolarization or the depolarization-mediated cell characteristic. In some embodiments, the light-activated ion channel is encoded by the nucleic acid sequence set forth as SEQ ID NO:1 or SEQ ID NO:3. In some embodiments, the amino acid sequence of the light-activated ion channel polypeptide comprises an amino acid sequence forth as SEQ ID NO:2, SEQ ID NO:4, SEQ ID NO:7, or SEQ ID NO:8. In some embodiments, the light-activated ion channel does not activate in response to contact with red light. In certain embodiments, a depolarization-mediated cell characteristic is an action potential. In some embodiments, a depolarization-mediated cell characteristic release of a neurotransmitter. In some embodiments, the cell is a nervous system cell, a cardiac cell, a circulatory system cell, a visual system cell, an auditory system cell, a muscle cell, or another excitable cell. In some embodiments, the cell is a mammalian cell. In certain embodiments, the cell also includes one, two, three, or more additional light-activated ion channel polypeptides, wherein at least one, two, three, four, or more of the additional light-activated ion channel polypeptides is activated by contact with light having a non-blue light wavelength and is not activated by contact with blue light having a wavelength in a range from about 450 nm to about 495 nm.

According to another aspect of the invention, methods of treating a disorder in a subject are provided. The methods include a) administering to a subject in need of such treatment, a therapeutically effective amount of any of the aforementioned embodiments of a blue-light-activated ion channel, to treat the disorder and b) contacting the cell with blue light and activating the light-activated ion channel in the cell under conditions sufficient to depolarize the cell, wherein depolarizing the cell treats the disorder in the subject. In some embodiments, the light-activated ion channel is administered in the form of a cell, wherein the cell expresses the light-activated ion channel, or in the form of a vector, wherein the vector comprises a nucleic acid sequence encoding the light-activated ion channel and the administration of the vector results in expression of the blue-light-activated ion channel in a cell in the subject. In some embodiments, the vector also includes a signal sequence. In some embodiments, the vector also includes a cell-specific promoter. In certain embodiments, the disorder is a neurological disorder, a visual system disorder, a circulatory system disorder, a musculoskeletal system disorder, or an auditory system disorder. In some embodiments, the method also includes administering an additional therapeutic composition to the subject. In some embodiments, depolarizing the cell modulates a depolarization-mediated cell characteristic. In some embodiments, a depolarization-mediated cell characteristic is an action potential. In certain embodiments, a depolarization-mediated cell characteristic release of a neurotransmitter. In some embodiments, the blue light-activated ion channel activates in response to light with a wavelength in a range from about 450 nm to about 495 nm. In some embodiments, the blue-light-activated ion channel is encoded by a nucleic acid sequence set forth as SEQ ID NO:1 or SEQ ID NO:3. In some embodiments, the amino acid sequence of the blue-light-activated ion channel is set forth as SEQ ID NO:2, SEQ ID NO:4, or SEQ ID NO:7, or SEQ ID NO:8. In certain embodiments, the blue light-activated ion channel does not activate in response to contact with light that is not blue light. In some embodiments, the cell is a nervous system cell, a neuron, a cardiac cell, a circulatory system cell, a visual system cell, an auditory system cell, or a muscle cell. In certain embodiments, the cell is a mammalian cell. In some embodiments, the cell also includes one, two, three, or more additional light-activated ion channel polypeptides, wherein at least one, two, three, four, or more of the additional light-activated ion channel polypeptides is activated by contact with light having a non-blue light wavelength and is not activated by contact with blue light having a wavelength in a range from about 450 nm to about 495 nm.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 2A is a graph showing current with contact with blue irradiance. FIG. 2B and 2C are graphs of $t_{on}$ at a 5 mW/mm$^2$ and 4.23 mW/mm$^2$ illumination, respectively and provide a comparision of results for ChR2, ChR64, and ChR68 light-activated ion channels. FIG. 2D shows the $t_{off}$ results from ChR86 light activated ion channel with blue irradiance at 4.23, 0.2, and 0.05 mW/mm$^2$.

FIGS. 3A-D provide photomicrographs and a table demonstrating trafficking, expression and light sensitivity of certain embodiments of light-activated ion channel polypeptides. FIG. 3A shows a photomicrographic image of a cultured neuron expressing wild-type SdChR. SdChR typically aggregated and formed puncta in the soma. Scale bar 25 µm. FIG. 3B shows a photomicrographic image of a neuron expressing SdChR with an additional trafficking sequence from Kir2.1 between the C-terminus of SdChR and the N-terminus of eGFP. This trafficking sequence substantially reduced intracellular puncta. Scale bar 25 µm. FIG. 3C shows a photomicrographic image of two neurons expressing CheRiff. Inclusion of the E154A mutation reduced red light sensitivity and reduced $\tau_{off}$ while maintaining excellent membrane trafficking Scale bar 25 µm. FIG. 3D is a table showing improvements in trafficking leading from ChR64 to CheRiff. *Scherffelia dubia* Channelrhodopsin (SdChR) had promising light sensitivity and a blue-shifted action spectrum appropriate for pairing with QuasArs; yet it did not traffic efficiently to the plasma membrane in rat hippocampal neurons. Of the three mutants, CheRiff demonstrated best results for trafficking, blue photocurrent, red photocurrent, and $t_{off}$ values.

FIG. 4A at top left shows components of channelrhodopsin current elicited by a step in blue light. $I_{pk}$ is the difference between baseline current and peak current. $t_{on}$ is the time between light onset and peak current. $\tau_{des}$ is the desensitization time constant determined by a single-exponential fit to the current decay after the peak. $I_{ss}$ is steady state photocurrent. $\tau_{off}$ is the channel closing time constant determined by a single-exponential fit to the current decay after the illumination ceases. FIG. 4A at top right shows peak ($I_{pk}$) and steady state ($I_{ss}$) photocurrents in neurons expressing CheRiff (n=10 cells), ChR2 H134R (n=6 cells), and ChIEF (n=6 cells). Photocurrents were measured in response to a 1 second 488 nm light pulse (50 mW/cm$^2$). CheRiff generated significantly larger peak photocurrent than ChR2 H134R (p<0.001) or ChIEF (p<0.001). CheRiff also had significantly larger steady state photocurrents than ChR2 H134R (p<0.001) or ChIEF (p<0.01). Bottom left: CheRiff had a significantly faster time to peak ($t_{on}$) when compared to ChR2 H134R (p<0.001) or ChIEF (p<0.001). Bottom middle: CheRiff desensitized with a time constant significantly slower than ChR2H134R (p<0.001) or ChIEF (p<0.001). FIG. 4A bottom right shows results when: $\tau_{off}$ was measured in response to a 5 ms illumination pulse (500 mW/cm$^2$). CheRiff (n=9 cells) had a significantly faster $\tau_{off}$ than ChR2 H134R (n=6 cells, p<0.05), and was comparable to ChIEF (n=6 cells, p=0.94). All channelrhodopsin comparisons were made on matched cultures, DIV 1.4-15. Expression was driven by a CaMKIIα promoter in identical plasmid backbones. See Examples section for details on cell culture. FIG. 4B top trace shows results indicating that under current-clamp (i=0) in a neuron expressing CheRiff, pulses of red light led to a small steady depolarization of 3.1±0.2 mV (n=5 cells). FIG. 4B bottom trace shows results indicating that under voltage-clamp (V=−65 mV), pulses of red light led to a small inward photocurrent of 14.3±3.1 pA (n=5 cells). Error bars represent s.e.m. Statistical significance determined by one way ANOVA with Dunnett's post hoc test. * p<0.05;  p<0.01; * p<0.001.

FIGS. 5A-E provide photomicrographic images and graphs showing application of CheRiff in cultured hippocampal neurons. FIG. 5A shows light micrographs (DIC) of *Scherffelia dubia* (strain CCAC 0053) in side view (top) and face view (bottom). Arrows mark eyespots (red). Scale bar 10 μm. FIG. 5B shows photomicrographic image of cultured rat hippocampal neuron expressing CheRiff-eGFP, imaged via eGFP fluorescence. Scale bar 25 μm. FIG. 5C shows photocurrents induced by CheRiff and by Channelrhodopsin2 H134R with illumination at 488 nm, 500 mW/cm$^2$. FIG. 5D provides a graph showing comparison of photocurrents as a function of illumination intensity in matched cultures expressing CheRiff (n=5 cells) or ChR2 H134R (n=5 cells). Illumination was either over the whole cell or confined to the soma. FIG. 5E provides a graph showing spiking fidelity as a function of stimulation frequency and illumination intensity in neurons expressing CheRiff (n=5 cells). Error bars in FIGS. 5D and E represent s.e.m.

BRIEF DESCRIPTION OF THE SEQUENCES

Figure 1:
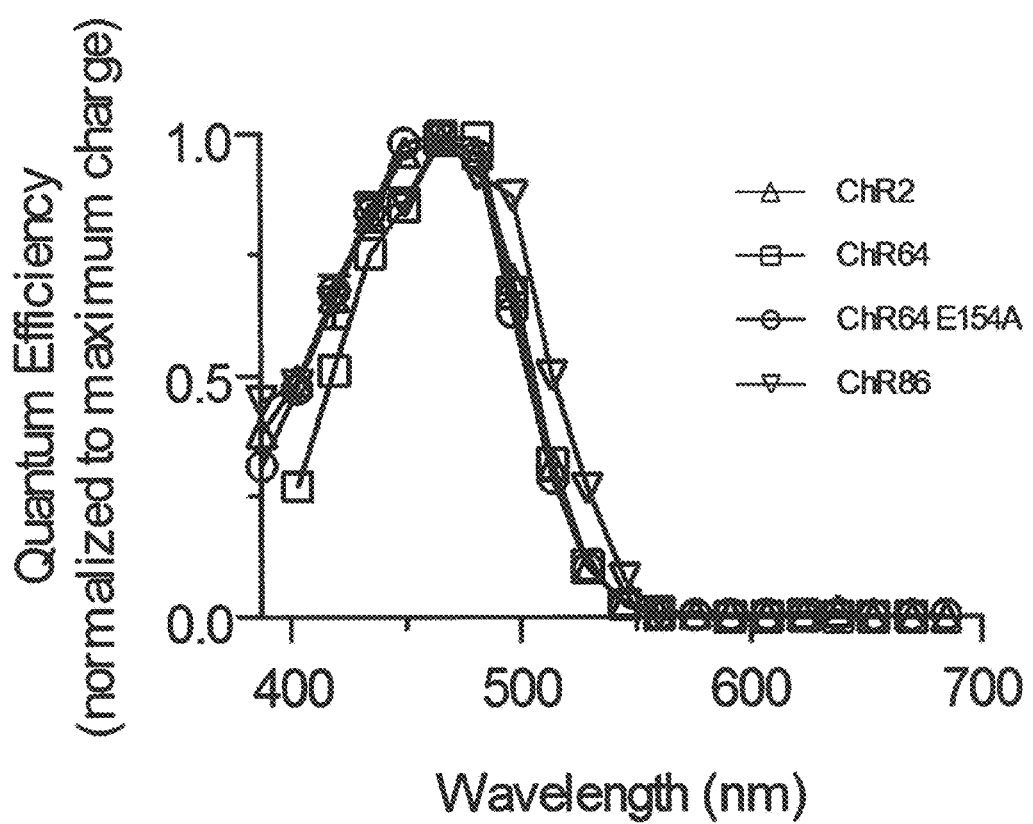
FIG. 1 shows action spectra recorded in HEK293 cells for ChR2, ChR64, ChR64 E154A, and ChR86 light-activated ion channel polypeptides when contacted with various wavelengths of light.
Figure 2A:
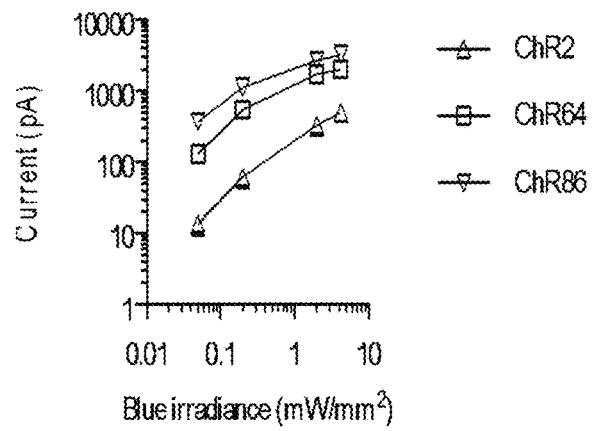
FIGS. 2A-D show graphs demonstrating blue light photocurrent and kinetic comparisons in cultured hippocampal neurons in which light-activated ion channels were expressed. Results from ChR2, ChR64, and ChR68 are shown.
Figure 2B:
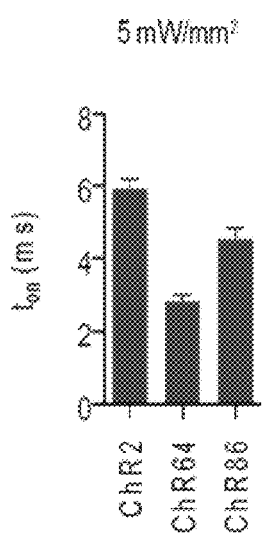
Figure 2C:
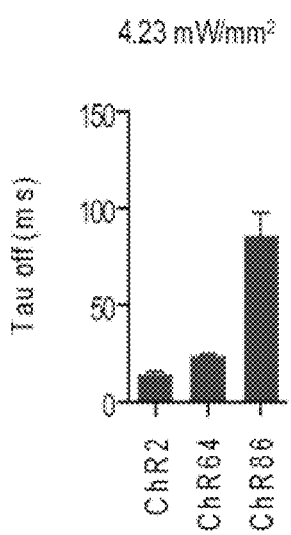
Figure 2D:
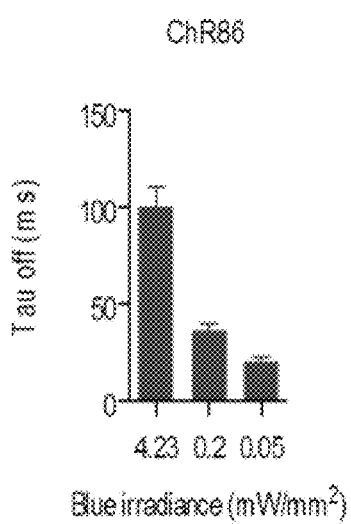

SEQ ID NO:1 is the mammalian codon-optimized DNA sequence that encodes the wild-type *Scherffelia dubia* channelrhodopsin, also referred to herein as ChR64 or SdChR:

atgggcggagctcctgctccagacgctcacagcgcccacctggaaacga ttctgccggaggcagtgagtaccatgccccagctggatatcaagtgaatc caccctaccaccccgtgcatgggtatgaggaacagtgcagctccatctac atctactatggggcctgtgggagcaggaaacagctaggggcttccagtg gtttgccgtgttcctgtctgccctgtttctggctttctacggctggcacg cctataaggccagcgtgggatggggaggaagtgtacgtgtgctccgtggag ctgatcaaagtgattctggagatctatttcgagttcaccagtcctgctat gctgttcctgtacggagggaacattacccccatggctgagatatgccgaat ggctgctgacatgtcccgtgatcctgattcatctgtctaacatcaccggc ctgagtgaggaatacaataagcggacaatggctctgctggtgtccgacct gggaactatttgcatgggagtgacagccgctctggccactgggtgggtga agtggctgttttactgtatcggcctggtgtatggaacccagacattctac aacgctggaatcatctacgtggagtcttactatatcatgcctgccggcgg ctgtaagaaactggtgctggccatgactgccgtgtactattctagttggc tgatgtttcccggcctgttcatctttgggcctgaaggcatgcacaccctg agcgtggctgggtccactattggccataccatcgccgacctgctgtccaa gaatatttggggactgctggggcacttcctgcggatcaaaattcacgagc atatcattatgtacggcgatatcaggagaccagtgagctcccagtttctg ggacgcaaggtggacgtgctggccttcgtgacagaggaagataaagtg.

SEQ ID NO: 2 is the amino acid sequence of the wild-type *Scherffelia dubia*, also referred to herein as ChR64 or SdChR:

MGGAPAPDAHSAPPGNDSAGGSEYHAPAGYQVNPPYHPVHGYEEQCSSIY

IYYGALWEQETARGFQWFAVFLSALFLAFYGWHAYKASVGWEEVYVCSVE

LIKVILEIYFEFTSPAMLFLYGGNITPWLRYAEWLLTCPVILIHLSNITG

LSEEYNKRTMALLVSDLGTICMGVTAALATGWVKWLFYCIGLVYGTQTFY

NAGIIYVESYYIMPAGGCKKLVLAMTAVYYSSWLMFPGLFIFGPEGMHTL

SVAGSTIGHTIADLLSKNIWGLLGHFLRIKIHEHIIMYGDIRRPVSSQFL

GRKVDVLAFVTEEDKV.

SEQ ID NO:3 is the mammalian codon-optimized DNA sequence that encodes wild-type *Chloromonas oogama* channelrhodopsin, also referred to herein as ChR86:

atgctgggaaacggcagcgccattgtgcctatcgaccagtgcttttgcct ggcttggaccgacagcctgggaagcgatacagagcagctggtggccaaca tcctccagtggttcgccttcggcttcagcatcctgatcctgatgttctac gcctaccagacttggagagccacttgcggttgggaggaggtctacgtctg ttgcgtcgagctgaccaaggtcatcatcgagttcttccacgagttcgacg accccagcatgctgtacctggctaacggacaccgagtccagtggctgaga tacgcagagtggctgctgacttgtcccgtcatcctgatccacctgagcaa cctgaccggcctgaaggacgactacagcaagcggaccatgaggctgctgg tgtcagacgtgggaaccatcgtgtggggagctacaagcgccatgagcaca ggctacgtcaaggtcatcttcttcgtgctgggttgcatctacggcgccaa caccttcttccacgccgccaaggtgtatatcgagagctaccacgtggtgc caaagggcagacctagaaccgtcgtgcggatcatggcttggctgttcttc ctgtcttggggcatgttccccgtgctgttcgtcgtgggaccagaaggatt cgacgccatcagcgtgtacggctctaccattggccacaccatcatcgacc tcatgagcaagaattgttgggcctgctgggacactatctgagagtgctg atccaccagcacatcatcatctacggcgacatccggaagaagaccaagat caacgtggccggcgaggagatggaagtggagaccatggtggaccaggagg acgaggagacagtg.

SEQ ID NO:4 is the amino acid sequence of wild-type *Chloromonas oogama* channelrhodopsin, also referred to herein as ChR86:

MLGNGSAIVPIDQCFCLAWTDSLGSDTEQLVANILQWFAFGFSILILMFY

AYQTWRATCGWEEVYVCCVELTKVIIEFFHEFDDPSMLYLANGHRVQWLR

YAEWLLTCPVILIHLSNLTGLKDDYSKRTMRLLVSDVGTIVWGATSAMST

GYVKVIFFVLGCIYGANTFFHAAKVYIESYHVVPKGRPRTVVRIMAWLFF

LSWGMFPVLFVVGPEGFDAISVYGSTIGHTIIDLMSKNCWGLLGHYLRVL

IHQHIIIYGDIRKKTKINVAGEEMEVETMVDQEDEETV.

SEQ ID NO:5 is the mammalian codon-optimized DNA sequence that encodes the wild-type Channelrhodopsin-2, (see: Boyden, E. et al., *Nature Neuroscience* 8, 1263-1268 (2005) and Nagel, G., et al. *PNAS* Nov. 25, 2003 vol. 100 no. 24 13940-13945), also referred to herein as ChR2:

atggactatgcggcgctttgtctgccgtcggacgcgaacttttgttcgt tactaatcctgtggtggtgaacgggtccgtcctggtccctgaggatcaat gttactgtgccggatggattgaatctcgcggcacgaacggcgctcagacc -continued

```
gcgtcaaatgtcctgcagtggcttgcagcaggattcagcattttgctgct gatgttctatgcctaccaaacctggaaatctacatgcggctgggaggaga tctatgtgtgcgccattgaaatggttaaggtgattctcgagttcttttt gagtttaagaatccctctatgctctaccttgccacaggacaccgggtgca gtggctgcgctatgcagagtggctgctcacttgtcctgtcatccttatcc acctgagcaacctcaccggcctgagcaacgactacagcaggagaaccatg ggactccttgtctcagacatcgggactatcgtgtgggggctaccagcgc catggcaaccggctatgttaaagtcatcttcttttgtcttggattgtgct atggcgcgaacacattttttcacgccgccaaagcatatatcgagggttat catactgtgccaaagggtcggtgccgccaggtcgtgaccggcatggcatg gctgttttcgtgagctggggtatgttcccaattctcttcattttggggc ccgaaggttttggcgtcctgagcgtctatggctccaccgtaggtcacacg attattgatctgatgagtaaaaattgttggggggttgttgggacactacct gcgcgtcctgatccacgagcacatattgattcacggagatatccgcaaaa ccaccaaactgaacatcggcggaacggagatcgaggtcgagactctcgtc gaagacgaagccgaggccgagccgtg.
```

SEQ ID NO: 6 is the amino acid sequence of the wild-type Channelrhodopsin-2, (see: Boyden, E. et al., *Nature Neuroscience* 8, 1263 - 1268 (2005) and Nagel, G., et al. *PNAS* Nov. 25, 2003 vol. 100 no. 24 13940-13945), also referred to herein as ChR2:

```
MDYGGALSAVGRELLFVTNPVVVNGSVLVPEDQCYCAGWIESRGTNGAQT

ASNVLQWLAAGFSILLLMFYAYQTWKSTCGWEEIYVCAIEMVKVILEFFF

EFKNPSMLYLATGHRVQWLRYAEWLLTCPVILIHLSNLTGLSNDYSRRTM

GLLVSDIGTIVWGATSAMATGYVKVIFFCLGLCYGANTFFHAAKAYIEGY

HTVPKGRCRQVVTGMAWLFFVSWGMFPILFILGPEGFGVLSVYGSTVGHT

IIDLMSKNCWGLLGHYLRVLIHEHILIHGDIRKTTKLNIGGTEIEVETLV

EDEAEAGAV.
```

SEQ ID NO:7 is the amino acid sequence of ChR64 with an E→A substitution at amino acid position 154:

```
MGGAPAPDAHSAPPGNDSAGGSEYHAPAGYQVNPPYHPVHGYEEQCSSIY

IYYGALWEQETARGFQWFAVFLSALFLAFYGWHAYKASVGWEEVYVCSVE

LIKVILEIYFEFTSPAMLFLYGGNITPWLRYAEWLLTCPVILIHLSNITG

LSEAYNKRTMALLVSDLGTICMGVTAALATGWVKWLFYCIGLVYGTQTFY

NAGIIYVESYYIMPAGGCKKLVLAMTAVYYSSWLMFPGLFIFGPEGMHTL

SVAGSTIGHTIADLLSKNIWGLLGHFLRIKIHEHIIMYGDIRRPVSSQFL

GRKVDVLAFVTEEDKV.
```

SEQ ID NO:8 is the amino acid sequence of ChR86 with a D→A substitution at amino acid position 124:

```
MLGNGSAIVPIDQCFCLAWTDSLGSDTEQLVANILQWFAFGFSILILMFY

AYQTWRATCGWEEVYVCCVELTKVIIEFFHEFDDPSMLYLANGHRVQWLR

YAEWLLTCPVILIHLSNLTGLKDAYSKRTMRLLVSDVGTIVWGATSAMST

GYVKVIFFVLGCIYGANTFFHAAKVYIESYHVVPKGRPRTVVRIMAWLFF

LSWGMFPVLFVVGPEGFDAISVYGSTIGHTIIDLMSKNCWGLLGHYLRVL

IHQHIIIYGDIRKKTKINVAGEEMEVETMVDQEDEETV.
```

SEQ ID NO:9 is the DNA sequence of the ER export sequence (also referred to herein as "ER2":

```
ttctgctacgagaatgaagtg.
```

SEQ ID NO:10 is the amino acid sequence of the ER export sequence (also referred to herein as "ER2":

```
FCYENEV.
```

SEQ ID NO:11 is the DNA sequence of KGC, which is a C terminal export sequence, (also referred to as a "trafficking sequence") from the potassium channel Kir2.1. It is also referred to herein as "TS":

```
aaatccagaattacttctgaaggggagtatatccctctggatcaaataga catcaatgtt.
```

SEQ ID NO:12 is the amino acid sequence of KGC, which is a C terminal export sequence, (also referred to as a "trafficking sequence") from the potassium channel Kir2.1. It is also referred to herein as "TS":

```
KSRITSEGEYIPLDQIDINV.
```

DETAILED DESCRIPTION

The invention in some aspects relates to the expression in cells of light-driven ion channel polypeptides that can be activated by contact with one or more pulses of light, which results in strong depolarization of the cell. Light-activated channels of the invention, also referred to herein as light-activated ion channels can be expressed in specific cells, tissues, and/or organisms and used to control cells in vivo, ex vivo, and in vitro in response to pulses of light of a suitable wavelength. This invention, in part, includes genes, DNA, mRNA, and proteins for light-gated ion channels, also referred to herein as light-activated channels. Expression of light-activated channels of the invention in genetically targeted cells enables millisecond-timescale generation of depolarizing current in response to pulses of light. Light-activated channels of the invention can be genetically expressed in specific cells (for example, through use of a virus) and then used to control electrical activity in cells in intact organisms, including, but not limited to humans, as well as cells in vitro, in response to pulses of light.

Channelrhodopsins are well known in the art as tools for optical control of membrane potential in electrically excitable cells. Light-activated channel polypeptides in some embodiments of the invention differ from prior channelrhodopsin tools in a number of ways, such as, but not limited to higher maximal photocurrents possible under saturating illumination and lower illumination intensity needed to trigger precisely timed neuronal action potentials. The ability to activate neurons at lower intensity allows use of light-activated ion channel polypeptides of the invention to be used in combination with one or more red-shifted light-activated pumps and channels (for example, but not limited to: Halo/NpHR, Arch, VChR1) without spurious activation of the red-shifted species by the blue light used to activate the light-activated ion channel polypeptides of the invention. In addition, in some embodiments, light-activated ion channel polypeptides of the invention may be expressed in combination with one or more other red-shifted reporters (e.g. Arch-based voltage indicators, R-GECO calcium indicator) without spurious activation of the reporter by the blue light used to activate the light-activated ion channel polypeptides of the invention. Certain embodiments of light-activated ion channel polypeptides of the invention can be used to activate neurons over larger regions, using lower power light sources, and with less risk of phototoxicity than was previously possible using alternative channelrhodopsins. An additional advantage of a light-activated ion channel polypeptide of the invention is its ability and use to trigger neuronal action potentials when only a sub-cellular region is illuminated. This capability permits studies of sub-cellular electrical dynamics to be performed using embodiments of light-activated ion channel polypeptides of the invention. In addition, light-activated ion channel polypeptides of the invention are not activated by, or are only minimally activated by contact with red light, further facilitating combination with red-shifted optical actuators and reporters.

In certain embodiments, the invention includes use of eukaryotic rhodopsins, such as from the genus *Scherffelia* or *Chloromonas*, including but not limited to rhodopsin from *Scherffelia dubia* ("ChR64", "SdChR") or *Chloromonas oogama* ("ChR86"), and variants thereof, to depolarize excitable cells. In certain embodiments of the invention, these light-activated ion channel polypeptides of the invention may be used to modify the pH of cells, or to introduce cations as chemical transmitters.

In some embodiments, light-activated ion channel polypeptides of the invention may be variants of ChR64 or ChR86 polypeptides. Thus, in part, the invention also includes targeted site-directed mutagenesis at specific amino acid residue(s) of channelrhodopsins to alter efficacy and kinetics of light-activated ion channel polypeptides of the invention. One mutation, which corresponds to D144 of ChR2 sequence, is demonstrated herein as improving channel turn-off kinetics while preserving photocurrent amplitude. Certain embodiments of light-activated ion channel polypeptides of the invention include specific amino acid changes, for example substitution. For example, an E154A mutation to ChR64 speeds up turn-off kinetics and preserves photocurrent amplitude. Similarly, a D124A single point mutation in the amino acid sequence of ChR86 also alters performance of this light-activated ion channel polypeptide of the invention when expressed and contacted with suitable light to activate the ion channel. A non-limiting example of an embodiment of a construct of a light-activated ion channel polypeptide is referred to herein as CheRiff. CheRiff includes the ChR64 sequence that has an E154A mutation and also includes the "TS" trafficking sequence. The construct is defined as ChR64(E154A)-TS-fluorophore. As used herein, the term "TS" is also referred to as the "KGC" sequence, which is set forth as: KSRITSEGEYIPLDQID-INV (SEQ ID NO:12).

It has been identified that not all channelrhodopsins can be expressed in cells and utilized to alter ion conductance through the channel, because many channelrhodopsins have been found to not traffick properly and/or function in mammalian cells. Many channelrhodopsins have now been examined and the light-activated ion channel polypeptides ChR64 and ChR86 have now been identified as functioning more effectively and better in mammalian cells than other classes of channelrhodopsins.

Light-activated ion channel polypeptides of the invention have been genetically express in excitable cells and the cells illuminated with light, which resulted in the rapid depolarization and optically evoked spiking of these cells in response to light. Thus, the light-activated ion channel polypeptides of invention may be utilized for light-control of cellular functions in vivo (including, but not limited to in human and non-human primates) and in vitro, and accordingly has broad-ranging impact on prosthetics, drug screening, and other biotechnological areas, non-limiting examples of which are discussed herein.

Light-activated ion channel polypeptides derived from *Scherffelia dubia* and *Chloromonas oogama* rhodopsin sequences, have now been identified.

Light-activated ion channel polypeptides of the invention are ion channels and may be expressed in a membrane of a cell. An ion channel is an integral membrane protein that forms a pore through a membrane and assist in establishing and modulating the small voltage gradient that exists across the plasma membrane of all cells and are also found in subcellular membranes of organelles such as the endoplasmic reticulum (ER), mitochondria, etc. When a light-activated ion channel polypeptide of the invention is activated by contacting the cell with appropriate light, the channel pore opens and permits conductance of ions such as sodium, potassium, calcium, etc. through the pore. It has been identified that light-activated ion channel polypeptides of the invention, are activated by contact with blue light. In some embodiments, a light-activated ion channel polypeptide of the invention is not activated by one or both of yellow light or red light. Certain embodiments of the invention may include a light-activated ion channel polypeptide that is minimally or not at all activated by at least one of red or yellow light. For example when contacted with a red or yellow light, a light-activated ion channel polypeptide may be activated not at all, or at least less than 1%, 2%, 3%, 4%, 5%, 6%, 7%, 8%, 9%, 10%, 11%, 12, 13%, 14%, 15%, 16%, 17%, 18%, 19%, or 20% of the level of activation of the light-activated ion channel polypeptide when contacted with blue light. Similarly, ion conduction through a light-activated ion channel polypeptide of the invention, when contacted with a red light may be at least 80%, 81%, 82%, 83%, 84%, 85%, 86%, 87%, 88%, 89%, 90%, 91%, 92%, 93%, 94%, 95%, 96%, 97%, 98%, 99%, or 100% less than the level of ion conduction of the light-activated ion channel polypeptide that is detected with the same method when the ion channel polypeptide is contacted with a blue light.

Similarly, ion conduction through a light-activated ion channel polypeptide of the invention, when contacted with a yellow light may be at least 80%, 81%, 82%, 83%, 84%, 85%, 86%, 87%, 88%, 89%, 90%, 91%, 92%, 93%, 94%, 95%, 96%, 97%, 98%, 99%, or 100% less than the level of ion conduction of the light-activated ion channel polypeptide that is detected with the same method when the ion channel polypeptide is contacted with a blue light.

In some embodiments of the invention, light-activated channels may be used to modify the transmembrane potential (and/or ionic composition) of cells (and/or their subcellular regions, and their local environment). For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of light-activated ion channel polypeptides of the invention in one, two, three, or more (e.g. a plurality) of cells in a tissue or organism, can result in depolarization of the single cell or the plurality of cells by contacting the light-activated ion channel polypeptides of the invention with light of suitable wavelength.

When expressed in a cell, some light-activated ion channel polypeptides of the invention can be activated by contacting the cell with blue light having a wavelength between about 450 nm to 495 nm. The light-activated ion channel polypeptides of the invention may also be activated when contacted with wavelengths of light that are outside this range, for example, contact with violet, green, yellow, orange, or red light may activate a light-activated ion channel polypeptide of the invention at some level. Thus, activation of a light-activated ion channel polypeptide of the invention, when contacted with a violet, green, yellow, or orange light may be at least 5%, 10%, 20%, 30%, 40%, 50%, 60%, 70%, 80%, 90%, 95%, 99%, or 100% less than the level of activation (e.g., which may in some embodiments be measured as ion conduction) of the light-activated ion channel polypeptide that is detected with the same method when the ion channel polypeptide is contacted with a blue light. Most effective and efficient level of activation of a light-activated ion channel polypeptide of the invention may occur when contacted with light in the range of 450 nm to 495 nm, 455 nm to 490 nm, 460 nm to 485 nm, 465 nm to 480 nm, or 455 nm to 485 nm. Thus, light-activated ion channel polypeptides of the invention are activated by contact with blue light, but may also be activated, at a less effective lower level of activation when contacted with other colors of light.

Contacting an excitable cell that includes a blue-light-activated ion channel polypeptide of the invention with a light in the blue spectrum strongly depolarizes the cell. For example, contact with light in a wavelength range such as between 450 nm and 495 nm, 455 nm and 490 nm, 460 nm and 485 nm, 465 nm and 480 nm, or 455 nm and 485 nm depolarizes the cell. Light-activated ion channel polypeptides of the invention have a peak wavelength sensitivity in the blue range and thus demonstrate a higher photocurrent at blue wavelengths than previously identified light-activated channels, for example, ChR2.

Light-activated ion channel polypeptides of the invention permit ion conductance and depolarization when contacted under suitable conditions with an appropriate wavelength of light. As will be understood by those in the art, the term "depolarized" used in the context of cells means an upward change in the cell voltage. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold an action potential (e.g. a spike) results. When a cell is depolarized by activating a light-activated ion channel polypeptide of the invention with an appropriate wavelength of light, the cell voltage becomes more positive than the baseline level, and an incoming signal may more easily raise the cell's voltage sufficiently to reach the threshold and trigger an action potential in the cell. It has been discovered that by contacting a cell expressing a light-activated ion channel polypeptide of the invention with light in the range between about 455 nm to about 485 nm, the voltage of the cell becomes less negative and may rise by at least about 20, 30, 40, 50, 60, 70, 80, 90, 100 mV (depending on the cell type) thus, depolarizing the cell.

Specific ranges of wavelengths of light useful to activate ion channels of the invention are provided and described herein. It will be understood that a light of appropriate wavelength for activation and will have a power and intensity appropriate for activation. It is well known in the art that light pulse duration, intensity, and power are parameters that can be altered when activating a channel with light. Thus, one skilled in the art will be able to adjust power, intensity appropriately when using a wavelength taught herein to activate a light-activated ion channel polypeptide of the invention. A benefit of a light-activated ion channel polypeptide of the invention, may be the ability to "tune" its response using an appropriate illumination variables (e.g., wavelength, intensity, duration, etc.) to activate the channel. Methods of adjusting illumination variables are well-known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19):8143-8. Epub 2007 May 1, each of which is incorporated herein by reference. Thus, it is possible to utilize a narrow range of one or more illumination characteristics to activate a light-activated ion channel polypeptide of the invention. This may be useful to illuminate a light-activated ion channel polypeptide that is co-expressed with one or more other light activated channels that can be illuminated with a different set of illumination parameters (for example, though not intended to be limiting, different wavelengths) for their activation, thus permitting controlled activation of a mixed population of light-activated channels. A light-activated ion channel polypeptide of the invention responds strongly to blue light and is activated, and therefore, because there are other channelrhodopsins that depolarize cells respond to green, red, or yellow light, in certain embodiments of the invention, a light-activated ion channel polypeptide of the invention can be expressed in a separate population of cells from a population of cells expressing one of these other opsins, allowing multiple colors of light to be used to excite these two populations of cells or neuronal projections from one site, at different times.

Light-activated ion channel polypeptides of the invention can be used either alone, using a selective light spectrum for activation and depolarization and can also be used in combination with other light-activated ion channels that utilize different wavelength of light for activation and depolarization, thus allowing two, three, four, or more different wavelengths of light to be used to depolarize different sets of cells in a tissue or organism by expressing channels with different activation spectra in different cells and then illuminating the tissue and/or organism with the appropriate wavelengths of light to activate the channels and depolarize the cells. In some embodiments of the invention, a light-activated ion channel of the invention is not activated by either or both of red or yellow light. This feature permits their use in clean non-perturbative imaging with another ion channel that is activated by red and/or yellow light (for example, R-GECO, Arch voltage imaging, etc.).

Thus, the invention, in some embodiments may include the expression of different types of ion channels, some of which are light activated ion channel polypeptides of the invention, and some that are not. Methods of the invention, in some embodiments, may include expression of light activated ion channels that are activated by different (e.g., non-overlapping) wavelengths of light. This permits simultaneous activation of one or more light-activated ion channel polypeptides of the invention using blue light range illumination, and imaging with a voltage/ion sensor channel polypeptide that is activated when contacted with light in the red and/or yellow range. As a non-limiting example, blue-light-activated ion channel polypeptides of the invention may be expressed in a cell and used in conjunction with ion channels that are activated by yellow and/or red light. Such use provides for activation of the light-activated ion channels of the invention by contact with light in the blue light range, and simultaneous monitoring of cell signal (e.g., calcium, voltage, etc.) using the ion channels activated by contact/illumination with red and/or yellow light.

In exemplary implementations, the invention comprises methods for preparing and using genes encoding light-activated ion channel polypeptides of the invention that have now been identified. The invention, in part, also includes isolated nucleic acids comprising sequences that encode light-activated ion channel polypeptides of the invention as well as vectors and constructs that comprise such nucleic acid sequences. In some embodiments the invention includes expression of polypeptides encoded by the nucleic acid sequences, in cells, tissues, and organisms.

Taxonomy and Sequence Sources

In particular, the present invention includes, in part, novel light-activated ion channel polypeptides and their use to depolarize cells. In some non-limiting embodiments of the invention one or more newly identified light-activated ion channel polypeptides may be expressed in cells. Some light-activated ion channel polypeptides of the invention have amino acid sequences derived from *Scherffelia dubia* or *Chloromonas oogama* rhodopsins that are naturally expressed. In certain aspects of the invention, the amino acid or encoding nucleic acid sequence of a polypeptide that is a variant of a *Scherffelia dubia* or *Chloromonas oogama* polypeptide or encoding nucleic acid sequence, may be referred to herein as being "derived" from the *Scherffelia dubia* or *Chloromonas oogama* amino acid sequence or nucleic acid sequence, respectively. Some embodiments of the invention include isolated wild-type or modified nucleic acid and/or amino acid rhodopsin sequences from *Scherffelia dubia* or *Chloromonas oogama*, and in some aspects, the invention also includes methods for their use. One skilled in the art will understand that a light-activated ion channel polypeptides of the invention can be identified based on sequence homology to a light-activated ion channel polypeptide sequence disclosed herein.

Light-activated ion channel polypeptides of the invention are transmembrane channel polypeptides that use light energy to open permitting ion conductance through their pore, thus altering the potential of the membrane in which they are expressed. A non-limiting example of an ion that can be moved through a pore of the invention includes a sodium ion, a potassium ion, a calcium ion, a proton, etc. Light-activated ion channel polypeptides of the invention can be activated by sustained light and/or by light pulses and by permitting ion conductance upon activation. Activation of light-activated ion channel polypeptides of the invention can depolarize cells and alter the voltage in cells and organelles in which they are expressed.

The wild-type and modified *Scherffelia dubia* or *Chloromonas oogama* rhodopsin nucleic acid and amino acid sequences used in aspects and methods of the invention are "isolated" sequences. As used herein, the term "isolated" used in reference to a polynucleotide, nucleic acid sequence or polypeptide sequence of a rhodopsin, it means a polynucleotide, nucleic acid sequence, or polypeptide sequence that is separate from its native environment and present in sufficient quantity to permit its identification or use. Thus, an isolated polynucleotide, nucleic acid sequence, or polypeptide sequence of the invention is a polynucleotide, nucleic acid sequence, or polypeptide sequence that is not part of, or included in its native host. For example, a nucleic acid or polypeptide sequence may be naturally expressed in a cell or organism of a member of the *Scherffelia* or *Chloromonas* genus, but when the sequence is not part of or included in a *Scherffelia* or *Chloromonas* cell or organism, it is considered to be isolated. Thus, a nucleic acid or polypeptide sequence of a *Scherffelia* or *Chloromonas* or other channelrhodopsin that is present in a vector, in a heterologous cell, tissue, or organism, etc., is an isolated sequence. The term "heterologous" as used herein, means a cell, tissue or organism that is not the native cell, tissue, or organism. The terms, "protein", "polypeptides", and "peptides" are used interchangeably herein. As used herein, the term "polynucleotide", "nucleic acid sequence" used in reference to sequences that encode a light-activated channel polypeptide of the invention may be used interchangeably.

Light-activated Ion Channel Sequences Including Modified Sequences

A light-activated ion channel polypeptide of the invention may comprise a wild-type polypeptide sequence or may be a modified polypeptide sequence. As used herein the term "modified" or "modification" in reference to a nucleic acid or polypeptide sequence refers to a change of one, two, three, four, five, six, or more amino acids in the sequence as compared to the wild-type sequence from which it was derived. For example, a modified polypeptide sequence may be identical to a wild-type polypeptide sequence except that it has one, two, three, four, five, or more amino acid substitutions, deletions, insertions, or combinations thereof. In some embodiments of the invention a modified sequence may include one, two, three, four, or more amino acid substitutions in a wild-type channelrhodopsin sequence.

It will be understood that sequences of light-activated ion channel polypeptides of the invention may be derived from various members of the *Scherffelia* genus or the *Chloromonas* genus or homologs thereof. Using standard methods for determining sequence homology one of ordinary skill in the art is able to identify additional channelrhodopsin sequences (including, but not limited to other *Scherffelia* or *Chloromonas* sequences) to identify homologous polypeptides that also function as light-activated ion channel polypeptides of the invention.

The invention, in some aspects also includes light-activated ion channel polypeptides having one or more substitutions or other modifications from those described herein. For example, sequences of light-activated ion channel polypeptides can be modified with one or more substitutions, deletions, insertions, or other modifications and can be tested using methods described herein for characteristics including, but not limited to: expression, cell localization, activation and depolarization in response to contact with light using methods disclosed herein. Exemplary modifications include, but are not limited to conservative amino acid substitutions, which will produce molecules having functional characteristics similar to those of the molecule from which such modifications are made. "Conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) [see, for example, Creighton, Proteins (1984)]. Light-activated ion channel polypeptides of the invention that include modifications, including but not limited to one, two, three, four, or more conservative amino acid substitutions can be identified and tested for characteristics including, but not limited to: expression, cell localization, activation and depolarization and depolarization-effects in response to contact with light using methods disclosed herein.

A light-activated ion channel polypeptide of the invention may include amino acid variants (e.g., polypeptides having a modified sequence) of a sequence set forth herein or another rhodopsin sequence. Modified light-activated ion channel polypeptide sequences may have at least about 75%, 80%, 85%, 90%, 95%, 96%, 97%, 98%, 99%, or 100% amino acid sequence similarity (also referred to as sequence identity) to the polypeptide sequence of a light-activated ion channel polypeptide disclosed herein, such as ChR64, ChR86, or variants thereof, etc. Similarity in this context means sequence similarity or identity. Such sequence similarity can be determined using standard techniques known in the art. Light-activated ion channel polypeptides of the present invention include light-activated ion channel polypeptide and nucleic acid sequences provided herein and variants that have at least about 75%, 80%, 85%, 90%, 95%, 96%, 97%, 98%, or 99% similarity to a provided sequence.

To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a light-activated channel polypeptide of the invention can be determined using art-known alignment and comparison methods for nucleic acids.

Light-activated ion channel polypeptides of the invention may be shorter or longer than the light-activated ion channel polypeptide sequences set forth herein. Thus, in some embodiments of the invention, included within the definition of light-activated ion channel polypeptides of the invention are full-length polypeptides or functional fragments thereof. In addition, nucleic acids of the invention may be used to obtain additional coding regions, and thus additional polypeptide sequences, using techniques known in the art.

In some aspects of the invention, substantially similar light-activated ion channel polypeptide sequences may have at least 80%, 85%, 90%, 91%, 92%, 93%, 94%, 95%, 96%, 97%, 98%, or 99% or 100% similarity to a light-activated ion channel polypeptide sequence disclosed herein, non-limiting examples of which include ChR64, ChR86, and variants thereof. Art-known alignment methods and tools can be used to align substantially similar sequences permitting positional identification of amino acids that may be modified as described herein to prepare a light-activated ion channel polypeptide of the invention. Non-limiting examples of variants of SEQ ID 2 and SEQ ID 4, include SEQ ID NO:7 and SEQ ID NO:8, respectively.

Sequence modifications can be in one or more of three classes: substitutions, insertions, or deletions. These modified sequences, (which may also be referred to as variants) ordinarily are prepared by site specific mutagenesis of nucleic acids in the DNA encoding a light-activated ion channel polypeptide of the invention, using cassette or PCR mutagenesis or other techniques known in the art, to produce DNA encoding the modified light-activated ion channel polypeptide, and thereafter expressing the DNA in recombinant cell culture. Where amino acid substitutions are made to a small fragment of a polypeptide, the substitutions can be made by directly synthesizing the polypeptide. In certain embodiments of the invention, activity of variant or fragment of a light-activated channel polypeptide or a variant of a light-activated channel polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

Amino acid sequence variants may be characterized by the predetermined nature of the variation, a feature that sets them apart from naturally occurring allelic or interspecies variation of the light-activated ion channel polypeptides of the invention. Modified light-activated ion channel polypeptides of the invention generally exhibit the same qualitative biological activity as the naturally occurring analogue, although variants can also be selected that have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed modified light-activated ion channel polypeptide screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues and in certain embodiments of the invention, 1, 2, 3, 4, 5, 6,7 8, 9, 10, 11, 12, 13, 14, 15, 16, 17, 18, 19, 20 or more substitutions can be made in the amino acid sequence of a light-activated ion channel polypeptide of the invention, for example, though not intended to be limiting, in a sequence set forth here as SEQ ID NO:2, SEQ ID NO:4, SEQ ID NO:7, or SEQ ID NO:8. Amino acid insertions in the amino acid sequence of a light-activated ion channel polypeptide of the invention, for example, though not intended to be limiting, in a sequence set forth here as SEQ ID NO:2, SEQ ID NO:4, SEQ ID NO:7, or SEQ ID NO:8 and may include insertion of 1, 2, 3, 4, 5, 6, 7 ,8, 9, 10, 11, 12, 13, 14, 15, 16, 17, 18, 19, or 20 amino acids, although larger insertions may be tolerated. Amino Acid deletions in the sequence of a light-activated ion channel polypeptide of the invention, for example, though not intended to be limiting, in a sequence set forth here as SEQ ID NO:2, SEQ ID NO:4, SEQ ID NO:7, or SEQ ID NO:8 may include deletions of 1, 2, 3, 4, 5, 6, 7, 8, 9, 10, 11, 12, 13, 14, 15, 16, 17, 18, 19, or 20 amino acids, although larger insertions may be tolerated.

Substitutions, deletions, insertions or any combination thereof may be used to arrive at a final modified light-activated ion channel polypeptide of the invention. Generally these changes are done on a few amino acids to minimize the alteration of the molecule. However, larger changes may be tolerated in certain circumstances.

Variants of light-activated ion channel polypeptides set forth herein, may exhibit the same qualitative light-activated ion channel activity as one or more of the sequences set forth herein, such as ChR64, ChR86, or variants thereof, but may show some altered characteristics such as altered photocurrent, stability, speed, compatibility, and toxicity, or a combination thereof. For example, the polypeptide can be modified such that it has an increased photocurrent and/or has less toxicity than another light-activated ion channel polypeptide.

A modified light-activated ion channel polypeptide of the invention can incorporate unnatural amino acids as well as natural amino acids. An unnatural amino acid can be included in a light-activated ion channel polypeptide of the invention to enhance a characteristic such as photocurrent, stability, speed, compatibility, or to lower toxicity, etc.

According to principles of this invention, the performance of light-activated ion channel polypeptides can be tuned for optimal use, including in the context of their use in conjunction with other molecules or optical apparatus. For example, in order to achieve optimal contrast for multiple-color stimulation, one may desire to either improve or decrease the performance of one molecule with respect to one another, by the appendage of trafficking enhancing sequences or creation of genetic variants by site-directed mutagenesis, directed evolution, gene shuffling, or altering codon usage. Light-activated ion channel polypeptides may have inherently varying spectral sensitivity. This may be used to advantage in vivo (where scattering and absorption will vary with respect to wavelength, coherence, and polarization), by tuning the linearity or non-linearity of response to optical illumination with respect to time, power, and illumination history.

In some embodiments, the invention includes the use of targeted site-directed mutagenesis at specific amino acid residues of channelrhodopsins including but not limited to residues of rhodopsins of *Scherffelia* and *Chloromonas*. Specific locations for single mutations can be identified and alone, or in combination with two or more additional mutations can be placed into a channelrhodopsin sequence and tested with respect to their activation and photocurrent amplitude. Thus, sequences of light-activated ion channel polypeptides of the invention, and/or similar channelrhodopsin sequences can be modified and the resulting polypeptides tested using methods disclosed herein.

Another aspect of the invention provides nucleic acid sequences that code for a light-activated ion channel polypeptide of the invention. It would be understood by a person of skill in the art that the light-activated ion channel polypeptides of the present invention can be coded for by various nucleic acids. Each amino acid in the protein is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for light-activated ion channel polypeptides of the invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein.

It is understood in the art that the codon systems in different organisms can be slightly different, and that therefore where the expression of a given protein from a given organism is desired, the nucleic acid sequence can be modified for expression within that organism. Thus, in some embodiments, a light-activated ion channel polypeptide of the invention is encoded by a mammalian-codon-optimized nucleic acid sequence, which may in some embodiments be a human-codon optimized nucleic acid sequence. An aspect of the invention provides a nucleic acid sequence that encodes a light-activated ion channel polypeptide that is optimized for expression with a mammalian cell. In certain aspects of the invention, a nucleic acid sequence is optimized for expression in a human cell.

Delivery of Light-activated Ion Channel Polypeptides

Delivery of a light-activated ion channel polypeptide to a cell and/or expression of a light-activated ion channel polypeptide in a cell can be done using art-known delivery means.

In some embodiments of the invention a light-activated ion channel polypeptide of the invention is included in a fusion protein. It is well known in the art how to prepare and utilize fusion proteins that comprise a polypeptide sequence. In certain embodiments of the invention, a fusion protein can be used to deliver a light-activated ion channel polypeptide to a cell and can also in some embodiments be used to target a light-activated ion channel polypeptide of the invention to specific cells or to specific cells, tissues, or regions in a subject. Targeting and suitable targeting sequences for delivery to a desired cell, tissue or region can be performed using art-known procedures.

It is an aspect of the invention to provide a light-activated ion channel polypeptide of the invention that is non-toxic, or substantially non-toxic in cells in which it is expressed. In the absence of light, a light-activated ion channel polypeptide of the invention does not significantly alter cell health or ongoing electrical activity in the cell in which it is expressed.

In some embodiments of the invention, a light-activated ion channel polypeptide of the invention is genetically introduced into a cellular membrane, and reagents and methods are provided for genetically targeted expression of light-activated ion channel polypeptides, including ChR64, ChR86, and variants thereof, etc. Genetic targeting can be used to deliver light-activated ion channel polypeptides to specific cell types, to specific cell subtypes, to specific spatial regions within an organism, and to sub-cellular regions within a cell. Genetic targeting also relates to the control of the amount of light-activated ion channel polypeptide expressed, and the timing of the expression.

Some embodiments of the invention include a reagent for genetically targeted expression of a light-activated ion channel polypeptide, wherein the reagent comprises a vector that contains the gene for the light-activated ion channel polypeptide.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert light-activated ion channel polypeptides into dividing and non-dividing cells and can insert light-activated ion channel polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising the gene for a light-activated ion channel polypeptide of the invention, such as ChR64, ChR86, or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a light-activated ion channel polypeptide in a wide variety of cell types—thus a promoter for a gene that is widely expressed in a variety of cell types, for example a "housekeeping gene" can be used to express a light-activated ion channel polypeptide in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER.

Methods of Use of Light-activated Ion Channel Polypeptides of the Invention

Light-activated ion channel polypeptides of the invention are well suited for targeting cells and specifically altering voltage-associated cell activities. In some embodiments of the invention, light-activated ion channel polypeptides of the invention can utilized to introduce cations into cells, thus activating endogenous signaling pathways (such as calcium dependent signaling), and then drugs are applied that modulate the response of the cell (using a calcium or voltage-sensitive dye). This allows new kinds of drug screening using just light to activate the channels of interest, and using just light to read out the effects of a drug on the channels of interest.

In certain aspects of the invention, a wild-type or modified *Scherffelia* or *Chloromonas* light-activated ion channel polypeptide of the invention may be used to sensitize cells to blue light. Such methods may be used to treat blindness and introduce visual perception to blue light.

In another aspect of the invention, a light-activated ion channel polypeptide of the invention may be used to decrease the pH of a cell in which it is expressed. Such a technique may be used to treat alkalosis.

Another aspect of the invention includes methods of using one or more light-activated proton pumps in conjunction with the use of light-activated ion channel polypeptides of the invention for the coupled effect of hyperpolarization and intracellular alkalinization. For example, both phenomena can induce spontaneous spiking in neurons by triggering hyperpolarization-induced cation currents or pH-dependent hyper-excitability. Another aspect of the invention is to utilize a light-activated ion channel polypeptide to generate sub-cellular voltage or pH gradients, particularly at synapses and in synaptic vesicles to alter synaptic transmission, and mitochondria to improve ATP synthesis.

Working operation of a prototype of this invention was demonstrated by genetically expressing light-activated ion channel molecules of the invention in excitable cells, illuminating the cells with suitable wavelengths of light, and demonstrating rapid depolarization of the cells in response to the light, as well as rapid release from depolarization upon cessation of light. Depending on the particular implementation, methods of the invention allow light control of cellular functions in vivo, ex vivo, and in vitro.

In non-limiting examples of methods of the invention, microbial channelrhodopsins are used in mammalian cells without need for any kind of chemical supplement, and in normal cellular environmental conditions and ionic concentrations. For example, genes encoding channelrhodopsins of *Scherffelia* and *Chloromonas* have been used in exemplary implementations of the invention. These sequences in humanized or mouse-optimized form allow depolarization at blue light wavelengths (e.g., light-activated ion channel polypeptides of the invention).

As used herein, the term "ion channel" means a transmembrane polypeptide that forms a pore, which when activated opens, permitting ion conductance through the pore across the membrane. Many ion channels do not express well in a cell and/or their expression may be toxic to the cell and reduce cell health. Thus it was necessary to prepare and screen numerous channelrhodopsin light-activated ion channel polypeptides to identify light-activated ion channels of the invention that can be expressed in cells without significantly reducing cell health and viability.

Light-activated ion channels of the invention have been found to be suitable for expression and use in mammalian cells without need for any kind of chemical supplement, and in normal cellular environmental conditions and ionic concentrations. Light-activated ion channel polypeptides of the invention have been found to differ from previously identified channels in that the light-activated ion channel polypeptides of the invention activate most efficiently at a wavelengths of light in the blue light range.

Cells and Subjects

A cell used in methods and with sequences of the invention may be an excitable cell or a non-excitable cell. A cell in which a light-activated ion channel polypeptide of the invention may be expressed and may be used in methods of the invention include prokaryotic and eukaryotic cells. Useful cells include but are not limited to mammalian cells. Examples of cells in which a light-activated ion channel polypeptide of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, etc.).

Non-limiting examples of cells that may be used in methods of the invention include: nervous system cells, cardiac cells, circulatory system cells, visual system cells, auditory system cells, secretory cells, endocrine cells, or muscle cells. In some embodiments, a cell used in conjunction with the invention may be a healthy normal cell, which is not known to have a disease, disorder or abnormal condition. In some embodiments, a cell used in conjunction with methods and channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Light-activated ion channel polypeptides of the invention may be expressed in cells from culture, cells in solution, cells obtained from subjects, and/or cells in a subject (in vivo cells). Light-activated ion channel polypeptides of the invention may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, rodent, fly or any other vertebrate or invertebrate organism.

Controls and Candidate Compound Testing

Light-activated ion channel polypeptides of the invention and methods using light-activated ion channel polypeptides of the invention can be utilized to assess changes in cells, tissues, and subjects in which they are expressed. Some embodiments of the invention include use of light-activated ion channel polypeptides of the invention to identify effects of candidate compounds on cells, tissues, and subjects. Results of testing a light-activated ion channel polypeptide of the invention can be advantageously compared to a control.

As used herein a control may be a predetermined value, which can take a variety of forms. It can be a single cut-off value, such as a median or mean. It can be established based upon comparative groups, such as cells or tissues that include the light-activated ion channel polypeptide of the invention and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a light-activated ion channel polypeptide to identify a candidate therapeutic agent or compound, a light-activated ion channel polypeptide of the invention may be expressed in an excitable cell in culture or in a subject and the excitable cell may be contacted with a light that activates the light-activated ion channel polypeptide and with a candidate therapeutic compound. In one embodiment, a test cell that includes a light-activated ion channel polypeptide of the invention can be contacted with a light that depolarizes the cell and also contacted with a candidate compound. The cell, tissue, and/or subject that include the cell can be monitored for the presence or absence of a change that occurs in the test conditions versus the control conditions. For example, in a cell, a change may be a change in the depolarization or in a depolarization-mediated cell characteristic in the test cell versus a control cell, and a change in depolarization or the depolarization-mediated cell characteristic in the test cell compared to the control may indicate that the candidate compound has an effect on the test cell or tissue that includes the cell. In some embodiments of the invention, a depolarization-mediated cell characteristic may be an action potential, pH change in a cell, release of a neurotransmitter, etc. and may in come embodiments, include a downstream effect on one or more additional cells, which occurs due to the depolarization of the cell that includes the light-activated ion channel polypeptide. Art-known methods can be used to assess depolarization and depolarization-mediated cell characteristics and changes to the depolarization or depolarization-mediated cell characteristics upon excitation of a light-activated ion channel polypeptide of the invention, with or without additional contact with a candidate compound.

Candidate-compound identification methods of the invention that are performed in a subject or in cultured or in vitro cells. Candidate-compound identification methods of the invention that are performed in a subject, may include expressing a light-activated ion channel polypeptide in the subject, contacting the subject with a light under suitable conditions to activate the light-activated ion channel polypeptide and depolarize the cell, and administering to the subject a candidate compound. The subject is then monitored to determine whether any change occurs that differs from a control effect in a subject. Candidate-compound identification methods of the invention that are performed in vitro may include expressing a light-activated ion channel polypeptide in a cell, which may or may not be a cultured cell, contacting the cell with a light under suitable conditions to activate the light-activated ion channel polypeptide and depolarize the cell, and contacting the cell with a candidate compound. The cell is then monitored to determine whether any change occurs that differs from a control effect in a cell. Thus, for example, a cell expressing the light-activated ion channel polypeptide can, in the presence of a candidate compound, be contacted with a light appropriate to activate the light-activated ion channel polypeptide. Contact of the light-activated ion channel polypeptide with the candidate compound may also occur at one or more time points prior to, at the same time as, or subsequent to contact with the light appropriate to activate the light-activated ion channel polypeptide. A result of such contact with the candidate compound can be measured and compared to a control value as a determination of the presence or absence of an effect of the candidate compound.

Methods of identifying effects of candidate compounds using light-activated ion channel polypeptides of the invention may also include additional steps and assays to further characterizing an identified change in the cell, tissue, or subject when the cell is contacted with the candidate compound. In some embodiments, testing in a cell, tissue, or subject can also include one or more cells that has a light-activated ion channel polypeptide of the invention, and that also has one, two, three, or more additional different light-activated ion channels, wherein at least one, two, three, four, or more of the additional light-activated ion channels is activated by contact with light having a different wavelength than used to activate the blue-light-activated ion channel polypeptide of the invention.

In a non-limiting example of a candidate drug identification method of the invention, cells that include a light-activated ion channel polypeptide of the invention are depolarized, thus triggering release of a neurotransmitter from the cell, and then drugs are applied that modulate the response of the cell to depolarization (determined for example using patch clamping methods or other suitable art-known means). Such methods enable new kinds of drug screening using just light to activate the channels of interest, and using just light to read out the effects of a drug on the channels and channel-containing cells of interest.

In some embodiments, light-activated ion channel polypeptides of the invention can be used in test systems and assays for assessing membrane protein trafficking and physiological function in heterologously expressed systems and the use of use of light-activated channels to depolarize a cell.

Methods of Treating

Some aspects of the invention include methods of treating a disorder or condition in a cell, tissue, or subject using light-activated ion channel polypeptides of the invention. Treatment methods of the invention may include administering to a subject in need of such treatment, a therapeutically effective amount of a light-activated ion channel polypeptide of the invention to treat the disorder. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be effective.

Administration of a light-activated ion channel polypeptide of the invention may include administration of a pharmaceutical composition that includes a cell, wherein the cell expresses the light-activated ion channel. Administration of a light-activated ion channel polypeptide of the invention may include administration of a pharmaceutical composition that includes a vector, wherein the vector comprises a nucleic acid sequence encoding the light-activated ion channel and the administration of the vector results in expression of the light-activated ion channel in a cell in the subject.

An effective amount of a light-activated ion channel polypeptide of the invention is an amount that increases the level of the light-activated ion channel polypeptide in a cell, tissue or subject to a level that is beneficial for the subject. An effective amount may also be determined by assessing physiological effects of administration on a cell or subject, such as a decrease in symptoms following administration. Other assays will be known to one of ordinary skill in the art and can be employed for measuring the level of the response to a treatment. The amount of a treatment may be varied for example by increasing or decreasing the amount of the light-activated ion channel polypeptide administered, by changing the therapeutic composition in which the light-activated ion channel polypeptide is administered, by changing the route of administration, by changing the dosage timing, by changing the activation amounts and parameters of a light-activated ion channel polypeptide of the invention, and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the light-activated ion channel polypeptide is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition to increase the level of a light-activated ion channel polypeptide, and/or to alter the length or timing of activation of a light-activated ion channel polypeptide in a subject (alone or in combination with other therapeutic agents) be used, that is, the highest safe dose or amount according to sound medical judgment. It will be understood by those of ordinary skill in the art, however, that a patient may insist upon a lower dose or tolerable dose for medical reasons, psychological reasons or for virtually any other reasons.

A light-activated ion channel polypeptide of the invention may be administered using art-known methods. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver light-activated ion channel polypeptides of the invention may be administered alone, in combination with each other, and/or in combination with other drug therapies, or other treatment regimens that are administered to subjects. A pharmaceutical composition used in the foregoing methods may contain an effective amount of a therapeutic compound that will increase the level of a light-activated ion channel polypeptide to a level that produces the desired response in a unit of weight or volume suitable for administration to a subject. In some embodiments of the invention, a pharmaceutical composition of the invention may include a pharmaceutically acceptable carrier.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. In certain embodiments of the invention, such preparations may contain salt, buffering agents, preservatives, compatible carriers, aqueous solutions, water, etc. When used in medicine, the salts may be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

One or more of a light-activated ion channel polypeptide or encoding polynucleotide of the invention, or a cell or vector comprising a light-activated ion channel polypeptide or encoding nucleic acid of the invention, may be administered, for example in a pharmaceutical composition, directly to a tissue. Direct tissue administration may be achieved by direct injection, and such administration may be done once, or alternatively a plurality of times. If administered multiple times, the polypeptides, polynucleotides, cells, and/or vectors may be administered via different routes. For example, the first (or the first few) administrations may be made directly into the affected tissue while later administrations may be systemic.

The dose of a pharmaceutical composition that is administered to a subject to increase the level of light-activated ion channel polypeptide in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a light-activated ion channel polypeptide of the invention (e.g., light wavelength, length of light contact, etc.) that has been administered to a subject can also be adjusted based on efficacy of the treatment in a particular subject. Parameters for illumination and activation of light-activated ion channel polypeptides of the invention that have been administered to a subject can be determined using art-known methods and without requiring undue experimentation.

Various modes of administration will be known to one of ordinary skill in the art that can be used to effectively deliver a pharmaceutical composition to increase the level of a light-activated ion channel polypeptide in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase light-activated ion channel polypeptide levels in a mammal other than a human; and administration and use of light-activated ion channel polypeptides of the invention, e.g. for testing purposes or veterinary therapeutic purposes, is carried out under substantially the same conditions as described above. It will be understood by one of ordinary skill in the art that this invention is applicable to both human and animals. Thus this invention is intended to be used in husbandry and veterinary medicine as well as in human therapeutics.

In some aspects of the invention, methods of treatment using a light-activated ion channel polypeptide of the invention are applied to cells including but not limited to a nervous system cell, a neuron, a cardiac cell, a circulatory system cell, a visual system cell, an auditory system cell, a muscle cell, or an endocrine cell, etc. Disorders and conditions that may be treated using methods of the invention include, injury, brain damage, degenerative neurological conditions (e.g., Parkinson's disease, Alzheimer's disease), seizure, vision loss, hearing loss, etc.

Disorders, Diseases and Conditions

Light-activated ion channel polypeptides of the invention may be used to target cells and membranes, and to alter voltage-associated cell activities. In some embodiments, a blue-light-activated ion channel polypeptides of the invention may be used to sensitize cells to blue light. Such methods may be used to treat blindness.

In another aspect of the invention, a light-activated ion channel polypeptide may be used to decrease the pH of a cell in which it is expressed. Such a technique may be used to treat alkalosis.

Another aspect of the invention includes methods of using light-activated proton pumps in conjunction with the use of light-activated ion channel polypeptides of the invention for the coupled effect of hyperpolarization and intracellular alkalinization. For example, both phenomena can induce spontaneous spiking in neurons by triggering hyperpolarization-induced cation currents or pH-dependent hyper-excitability.

In some embodiments, methods and light-activated ion channel polypeptides of the invention may be used for the treatment of visual system disorders, for example to treat vision reduction or loss. A light-activated ion channel polypeptide of the invention may be administered to a subject who has a vision reduction or loss and the cell that expresses the light-activated ion channel polypeptide of the invention can function as light-sensitive cells in the visual system, thereby permitting a gain of visual function in the subject.

The present invention in some aspects, includes preparing nucleic acid sequences and polynucleotide sequences; expressing in cells and membranes polypeptides encoded by the prepared nucleic acid and polynucleotide sequences; illuminating the cells and/or membranes with suitable light, and demonstrating rapid depolarization of the cells and/or a change in conductance across the membrane in response to light, as well as rapid release from depolarization upon cessation of light. The ability to controllably alter voltage across membranes and cell depolarization with light has been demonstrated. The present invention enables light-control of cellular functions in vivo, ex vivo, and in vitro, and the light activated ion channels of the invention and their use, have broad-ranging applications for drug screening, treatments, and research applications, some of which are describe herein.

In illustrative implementations of this invention, the ability to optically perturb, modify, or control cellular function offers many advantages over physical manipulation mechanisms. These advantages comprise speed, non-invasiveness, and the ability to easily span vast spatial scales from the nanoscale to macroscale.

The reagents use in the present invention (and the class of molecules that they represent), allow, at least: currents activated by blue light wavelengths which may differ in spectra from older molecules (opening up multi-color control of cells).

EXAMPLES

Example 1

Introduction

The present invention describes the use of light-gated channels to modify the transmembrane potential (and/or ionic composition) of cells (and/or their sub-cellular regions, and their local environment). In particular, the use of inwardly rectifying cationic channels will depolarize cells by moving positively charged ions from the extracellular environment to the cytoplasm. Under certain conditions, their use can decrease the intracellular pH (and/or increase the intracellular cation concentration) or increase the extracellular pH (and/or decrease the extracellular cation concentration). Compared to the currently reported natural gene sequences used to depolarize neurons in the prior art [see for example, Zhang, F. et al. *Nature* 446, 633-639, (2007) and Han, X. & Boyden, E. S. *PloS one* 2, e299, (2007), the content of each of which is incorporated herein by reference] (this disclosure notwithstanding), ChR64 and ChR86 have demonstrably improved photocurrent generation in response to blue light.

Experiments were performed in which the gene derived from either *Scherffelia dubia* or *Chloromonas oogama* was expressed in a cell. The gene derived from *Scherffelia dubia* encoded the amino acid sequence set forth herein as SEQ ID NO:2, and is referred to herein as ChR64, which is encoded by mammalian codon-optimized DNA sequence set forth herein as SEQ ID NO:1. The gene derived from *Chloromonas oogama* encoded the amino acid sequence set forth herein as SEQ ID NO:4, and is referred to herein as ChR86, which is encoded by the mammalian codon-optimized DNA sequence set forth herein as SEQ ID NO:3. In the experiments, ChR64 and ChR86 were expressed in cells as described as follows. [Also, for descriptions and examples of experimental methods and procedures see Chow, B. Y. et al. *Nature* 463, 98-102, (2010), the content of which is incorporated by reference herein].

Methods (1) The opsin gene was cloned into a lentiviral or adeno-associated virus (AAV) packaging plasmid, or another desired expression plasmid, and then GFP was cloned downstream of the preferred gene, eliminating the stop codon of the opsin gene, thus creating a fusion protein.

(2) The viral or expression plasmid contained either a strong ubiquitous promoter, a cell-specific promoter, or a strong general promoter followed by one more logical elements (such as a lox-stop-lox sequence, which would be removed by Cre recombinase selectively expressed in cells in a transgenic animal, or in a second virus, thus enabling the strong general promoter to then drive the gene [for descriptions and examples of experimental methods and procedures see for example, Atasoy, D., et al., *J. Neurosci* 28, 7025-7030, (2008) and Kuhlman, S. J. & Huang, Z. J. *PLoS ONE* 3, e2005, (2008), the content of each of which is incorporated by reference herein].

(3) If using a viral plasmid, the viral vector was synthesized using the viral plasmid, using standard techniques [for descriptions and examples of experimental methods and procedures see for example, Sena-Esteves, M., et al., *J Virol Methods* 122, 131-139, (2004), the content of which is incorporated by reference herein].

(4) If using a virus, as appropriate for gene therapy (over 600 people have been treated with AAV carrying various genetic payloads to date, in 48 separate clinical trials, without a single adverse event), the virus is injected using a small needle or cannula into the area of interest, thus delivering the gene encoding the opsin fusion protein into the cells of interest. If using another expression vector, directly electroporate or inject that vector into the cell or organism (for acutely expressing the opsin, or making a cell line, or a transgenic mouse or other animal).

(5) Illuminate with light. For ChR64 and ChR86, peak illumination wavelengths with which the expressed light-activated ion channel polypeptides were contacted were 470 nm±15 nm.

(6) The above wavelengths illustrate typical modes of operation, but are not meant to constrain the protocols that can be used. Either narrower or broader wavelengths, or differently-centered illumination spectra, are used. For prosthetic uses, the devices used to deliver light may be implanted for examples using LED and fiber arrays using standard procedures [for descriptions and examples of experimental methods and procedures see for example Campagnola, L., et al., *J Neurosci Methods* 169, 27-33, (2008), the content of which is incorporated by reference herein.]. For drug screening, a xenon lamp or LED can be used to deliver the light.

The performance of the above example may be changed by expressing a light-activated ion channel polypeptide that is altered from either ChR64 or ChR86 by site-directed mutagenesis, such as the E154A single mutation to ChR64 and the D124A single point mutation to ChR86. The performance of a light-activated ion channel polypeptide of the invention may also be improved by appending C-terminal peptide sequences to affect cellular trafficking, such as the C terminal Kir2.1 signal sequence (denoted as "KGC") [see Munoz-Jordan, J. L. et al. *J. Virol.* 79, 8004-8013, (2005), the content of which is incorporated by reference herein] (amino acid sequence: KSRITSEGEYIPLDQIDINV SEQ ID NO:12; DNA sequence: aaatccagaattacttctgaaggggag-tatatccctctggatcaaatagacatcaatgtt (SEQ ID NO:11).

Methods of Use of Light Activated Ion Channel Polypeptides

It has now been demonstrate that ChR64 and ChR86 can be activated with low blue light powers and have no red-light sensitivity. By using these blue-peaked channelrhodopsins together with red-shifted fluorescent sensors, it is possible to simultaneously image physiological response (e.g. voltage, ion, etc.) and optically depolarize cells using low blue light powers, without interference in the imaging channel. This simultaneous imaging and optical depolarization is particularly useful for feedback control and interrogation of cellular and network physiology.

The performance of the above said molecules or classes of molecules can be tuned for optimal use, particularly in context of their use in conjunction with other molecules or optical apparatus. For example, to achieve optimal contrast for simultaneous optical depolarization and imaging, one may desire to either improve or decrease the performance of one molecule with respect to another, by the appendage of trafficking enhancing sequences or creation of genetic variants by site-directed mutagenesis, directed evolution, gene shuffling, or altering codon usage. Molecules or classes of molecules may have inherently varying spectral sensitivity that may be functionally advantageous in vivo (where scattering and absorption will vary with respect to wavelength, coherence, and polarization), by tuning the linearity or non-linearity of response to optical illumination with respect to time, power, and illumination history.

The ability to introduce cations into cells, thus activating endogenous signaling pathways (such as calcium dependent signaling), and then applying drugs that modulate the response of the cell (using a calcium or voltage-sensitive dye as the readout of cellular electrophysiology), is also enabled by this disclosure. This enables new kinds of drug screening using just light to activate the channels of interest, and using just light to read out the effects of a drug on the channels of interest.

Another aspect of the invention is the use of light-activated channel to decrease the pH of the cell. Such a technique may be used to treat alkalosis.

Another aspect of the invention is to generate sub-cellular voltage or pH gradients, particularly at synapses and in synaptic vesicles to alter synaptic transmission; and in mitochondria to modulate ATP synthesis.

Another aspect of the invention is the various compositions of matter that have been prepared including, but not limited to: (1) plasmids encoding for the above genes; (2) lentiviruses carrying payloads encoding for the above described genes; (3) adeno-associated viruses carrying payloads encoding for the above-described genes; (4) cells expressing the above-described genes; and (5) animals expressing the above-described genes.

Example 2

Studies were performed to prepare sequences and to express light-activated ion channels in cells, tissues, and subjects. Non-limiting exemplary methods are set forth Example 1. General methods also applicable to light-activated channel molecules and methods for their use are disclosed in publications such as US Published Application No. 2010/0234273, US Published Application No. 20110165681, Chow B Y, et. al. *Methods Enzymol.* 2011; 497:425-43; Chow, B Y, et al. *Nature* 2010 Jan 7; 463(7277): 98-102, the content of each of which is incorporated by reference herein.

Studies were performed to prepare sequences and to express light-activated ion channels in cells, tissues, and subjects. Non-limiting exemplary methods are set forth below.

Plasmid Construction and Site Directed Mutagenesis

Opsins were mammalian codon-optimized, and synthesized by Genscript (Genscript Corp., NJ). Opsins were fused in frame, without stop codons, ahead of GFP (using BamHI and AgeI) in a lentiviral vector containing the CaMKII promoter, enabling direct neuron transfection, HEK cell transfection (expression in HEK cells is enabled by a ubiquitous promoter upstream of the lentiviral cassette), and lentivirus production and transfection.

Amino acid sequences of various opsins were as follows: ChR64 (SEQ ID NO:2); ChR86 (SEQ ID NO:4); ChR64 with E154A substitution (SEQ ID NO:7); ChR86 with D124A substitution (SEQ ID NO:8).

The 'ER2' ER export sequence corresponded to amino acid sequence FCYENEV, DNA sequence ttctgctacgagaatgaagtg. The 'KGC' signal sequence corresponded to amino acid sequence KSRITSEGEYIPLDQIDINV (SEQ ID NO:12), DNA sequence of KGC signal sequence: aaatccagaattacttctgaaggggagtatatccctctggatcaaatagacatcaatgtt (SEQ ID NO:11).

Neuron Culture, Transfection, Infection, and Imaging

All procedures involving animals were in accordance with the National Institutes of Health Guide for the care and use of laboratory animals and approved by the Massachusetts Institute of Technology Animal Care and Use Committee. Swiss Webster or C57 mice (Taconic, Hudson, N.Y. or The Jackson Laboratory, Bar Harbor, Me.) were used. For hippocampal cultures, hippocampal regions of postnatal day 0 or day 1 mice were isolated and digested with trypsin (1 mg/ml) for ~12 min, and then treated with Hanks solution supplemented with 10-20% fetal bovine serum and trypsin inhibitor (Sigma-Aldrich, St. Louis, Mo.). Tissue was then mechanically dissociated with Pasteur pipettes, and centrifuged at 1000 rpm at 4° C. for 10 min. Dissociated neurons were plated at a density of approximately four hippocampi per 20 glass coverslips, coated with Matrigel (BD Biosciences, Sparks, Md.). For cortical cultures, dissociated mouse cortical neurons (postnatal day 0 or 1) were prepared as previously described, and plated at a density of 100-200k per glass coverslip coated with Matrigel (BD Biosciences, Sparks, Md.). Cultures were maintained in Neurobasal Medium supplemented with B27 [Invitrogen, (Life Technologies Corporation, Carlsbad, Calif.)] and glutamine. Hippocampal and cortical cultures were used interchangeably; no differences in reagent performance were noted.

Neurons were transfected at 3-5 days in vitro using calcium phosphate [Invitrogen, (Life Technologies Corporation, Carlsbad, Calif.)]. GFP fluorescence was used to identify successfully transfected neurons. Alternatively, neurons were infected with 0.1-3 µl of lentivirus or adeno-associated virus (AAV) per well at 3-5 days in vitro.

HEK 293FT Cell Culture and Transfection

HEK 293FT cells [Invitrogen, (Life Technologies Corporation, Carlsbad, Calif.)] were maintained between 10-70% confluence in D10 medium (Cellgro, Manassas, Va.) supplemented with 10% fetal bovine serum [Invitrogen, (Life Technologies Corporation, Carlsbad, Calif.)], 1% penicillin/streptomycin (Cellgro, Manassas, Va.), and 1% sodium pyruvate (Biowhittaker, Walkersville, Md.)). For recording, cells were plated at 5-20% confluence on glass coverslips coated with Matrigel (BD Biosciences, Sparks, Md.). Adherent cells were transfected approximately 24 hours post-plating either with TransLT 293 lipofectamine transfection kits (Mirus, Madison, Wis.) or with calcium phosphate transfection kits [Invitrogen, (Life Technologies Corporation, Carlsbad, Calif.)], and recorded via whole-cell patch clamp between 36-72 hours post-transfection.

Lentivirus Preparation

HEK293FT cells [Invitrogen, (Life Technologies Corporation, Carlsbad, Calif.)] were transfected with the lentiviral plasmid, the viral helper plasmid p48.74, and the pseudotyping plasmid pMD2.G. The supernatant of transfected HEK cells containing virus was then collected 48 hours after transfection, purified, and then pelleted through ultracentrifugation. Lentivirus pellet was resuspended in phosphate buffered saline (PBS) and stored at −80° C. until further usage in vitro or in vivo. The estimated final titer is approximately $10^9$ infectious units/mL.

In vitro Whole Cell Patch Clamp Recording & Optical Stimulation

Whole cell patch clamp recordings were made using a Multiclamp 700B amplifier, a Digidata 1440 digitizer, and a PC running pClamp (Molecular Devices, Sunnyvale, Calif.). Neurons were bathed in room temperature Tyrode containing 125 mM NaCl, 2 mM KCl, 3 mM $CaCl_2$, 1 mM $MgCl_2$, 10 mM HEPES, 30 mM glucose, 0.01 mM NBQX and 0.01 mM GABAzine. The Tyrode pH was adjusted to 7.3 with NaOH and the osmolarity was adjusted to 300 mOsm with sucrose. HEK cells were bathed in a Tyrode bath solution identical to that for neurons, but lacking GABAzine and NBQX. Borosilicate glass pipettes (Warner Instruments, Hamden, Conn.) with an outer diameter of 1.2 mm and a wall thickness of 0.255 mm were pulled to a resistance of 3-9 MΩ with a P-97 Flaming/Brown micropipette puller (Sutter Instruments, Novato, Calif.) and filled with a solution containing 125 mM K-gluconate, 8 mM NaCl, 0.1 mM $CaCl_2$, 0.6 mM MgCl2, 1 mM EGTA, 10 mM HEPES, 4 mM Mg-ATP, and 0.4 mM Na-GTP. The pipette solution pH was adjusted to 7.3 with KOH and the osmolarity was adjusted to 298 mOsm with sucrose. Access resistance was 5-30 MΩ, monitored throughout the voltage-clamp recording. Resting membrane potential was ~31 60 mV for neurons and ~−30 mV for HEK 293FT cells in current-clamp recording.

Photocurrents were measured with 500 ms light pulses in neurons voltage-clamped at −60 mV, and in HEK 293FT cells voltage-clamped at −30 mV. Light-induced membrane hyperpolarizations were measured with 500 ms light pulses in cells current-clamped at their resting membrane potential. Light pulses for all wavelengths except 660 nm and action spectrum characterization experiments were delivered with a DG-4 optical switch with 300 W xenon lamp (Sutter Instruments, Novato, Calif.), controlled via TTL pulses generated through a Digidata signal generator. Green light was delivered with a 575±25 nm bandpass filter (Chroma, Bellows Falls, Vt.) and a 575±7.5 nm bandpass filter (Chroma, Bellows Falls, Vt.). Action spectra were taken with a Till Photonics Polychrome V, 150 W Xenon lamp, 15 nm monochromator bandwidth.

Data was analyzed using Clampfit (Molecular Devices, Sunnyvale, Calif.) and MATLAB (Mathworks, Inc., Natick, Mass.).

Example 3

ChR64 (SEQ ID NO:2); ChR86 (SEQ ID NO:4); ChR64 with E154A substitution (SEQ ID NO:7); ChR86 with D124A substitution (SEQ ID NO:8) and ChR2 including a ChR2 H134R substitution mutant were expressed in HEK293 cells using methods described in Examples. Normalized action spectrum were recorded in the cells under physiological conditions with the voltage clamped to −65mV. Equal photon flux was used at each wavelength.

FIG. 1 shows action spectra recorded in HEK293 cells.
FIG. 2 shows blue light photocurrent and kinetic comparisons in cultured hippocampal neurons.
FIG. 3 shows improvements in trafficking leading from ChR64 to CheRiff FIG. 3A shows photomicrographic image of a cultured neuron expressing wild-type SdChR. SdChR typically aggregated and formed puncta in the soma. FIG. 3B shows photomicrographic image of a neuron expressing SdChR with an additional trafficking sequence from Kir2.1 between the C-terminus of SdChR and the N-terminus of eGFP. This trafficking sequence substantially reduced intracellular puncta. FIG. 3C shows photomicrographic image of two neurons expressing CheRiff. Inclusion of the E154A mutation reduced red light sensitivity and reduced $\tau_{off}$ while maintaining excellent membrane trafficking FIG. 3D shows data demonstrating that there were improvements in trafficking leading from ChR64 to CheRiff. *Scherffelia dubia* Channelrhodopsin (SdChR) had promising light sensitivity and a blue-shifted action spectrum appropriate for pairing with QuasArs; yet it did not traffic efficiently to the plasma membrane in rat hippocampal neurons.

Figure 4A:
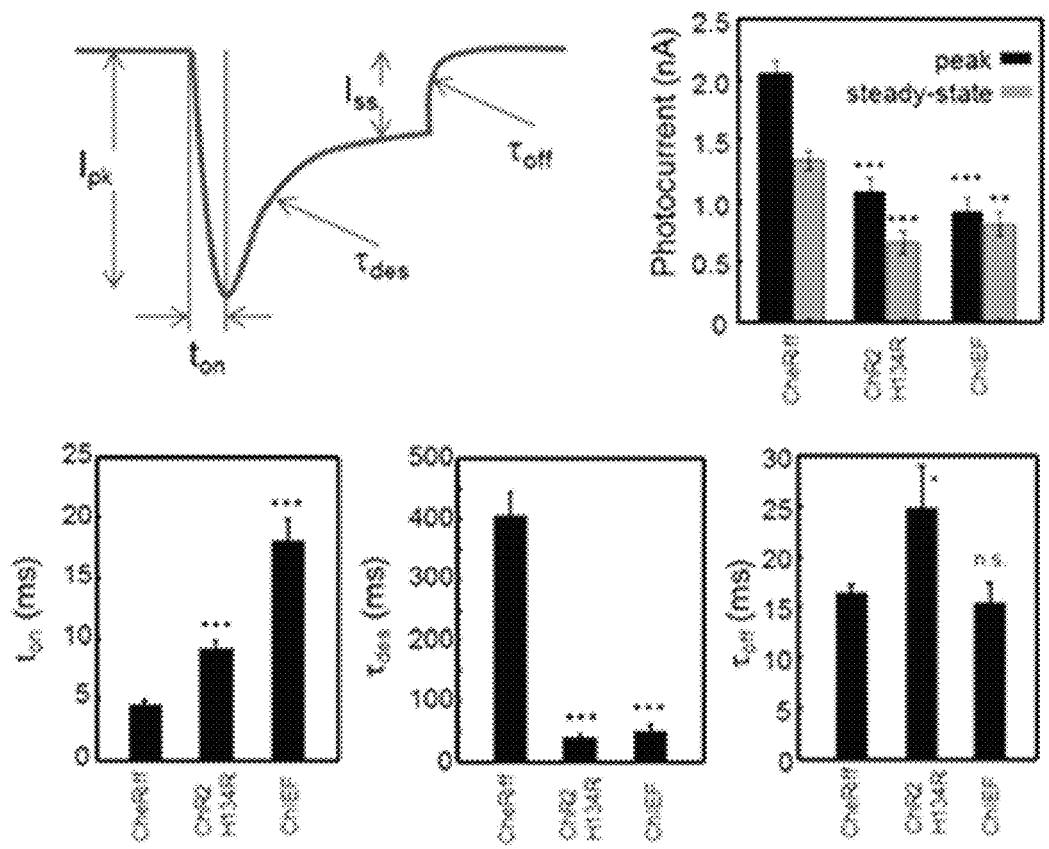
FIGS. 4A and B show traces and graphs demonstrating spectroscopic and kinetic properties of CheRiff.
Figure 4B:
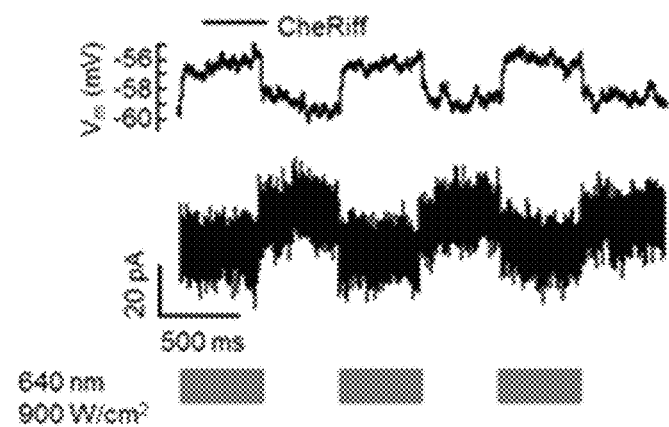
FIG. 4B shows activation of CheRiff by red light used for imaging Arch-based voltage indicators (640 nm, 900 W/cm$^2$).

FIG. 4 shows spectroscopic and kinetic properties of CheRiff. FIG. 4A at top left shows Components of channelrhodopsin current elicited by a step in blue light. $I_{pk}$ is the difference between baseline current and peak current. $t_{on}$ is the time between light onset and peak current. $\tau_{des}$ is the desensitization time constant determined by a single-exponential fit to the current decay after the peak. $I_{ss}$ is steady state photocurrent. $\tau_{off}$ is the channel closing time constant determined by a single-exponential fit to the current decay after the illumination ceases. FIG. 4A at top right shows peak ($I_{pk}$) and steady state ($I_{ss}$) photocurrents in neurons expressing CheRiff (n=10 cells), ChR2 H134R (n=6 cells), and ChIEF (n=6 cells). Photocurrents were measured in response to a 1 second 488 nm light pulse (500 mW/cm$^2$). CheRiff generated significantly larger peak photocurrent than ChR2 H134R (p<0.001) or ChIEF (p<0.001). CheRiff also had significantly larger steady state photocurrents than ChR2 H134R (p<0.001) or ChIEF (p<0.01). Bottom left: CheRiff had a significantly faster time to peak ($t_{on}$) when compared to ChR2 H134R (p<0.001) or ChIEF (p<: 0.001). Bottom middle: CheRiff desensitized with a time constant significantly slower than ChR2 H1.34R (p<0.001) or ChIEF (p<0.001). FIG. 4A bottom right shows results when $\tau_{off}$ was measured in response to a 5 ms illumination pulse (500 mW/cm$^2$). CheRiff (n=9 cells) had a significantly faster $\tau_{off}$ than ChR2 H134R (n=6 cells, p<0.05), and was comparable to ChIEF (n=6 cells, p=0.94). All channelrhodopsin comparisons were made on matched cultures, DIV 14-15. Expression was driven by a CaMKIIα promoter in identical plasmid backbones. See Examples section for details on cell culture. FIG. 4B shows activation of CheRiff by red light used for imaging Arch-based voltage indicators (640 nm, 900 W/cm$^2$). FIG. 4B top shows results indicating that under current-clamp (i=0) in a neuron expressing CheRiff, pulses of red light led to a small steady depolarization of 3.1±0.2 mV (n=5 cells). FIG. 4B bottom shows results indicating that under voltage-clamp (V=−65 mV), pulses of red light led to a small inward photocurrent of 14.3±3.1 pA (n=5 cells).

Table 1 contains a summary of the comparisons between CheRiff, ChR2 H134R, and ChIEF [For additional information on ChIEF, see Lin, J. Y., et al., *Biophysical Journal* (2009) Vol, 96, Issue 5, 4 March, pp 1803-1814, the content of which is incorporated by reference herein].

TABLE 1

Comparison of CheRiff, ChIEF, and ChR2 H134R.

| ChR variant | $I_{max}$ (nA; 488 nm, 0.5 W/cm$^2$) Peak | $I_{max}$ (nA; 488 nm, 0.5 W/cm$^2$) Steady state | $t_{on}$ (ms) | $\tau_{des}$ (ms) | $\tau_{off}$ (ms) | Red photocurrent (pA; 640 nm, 300 W/cm$^2$) | Red light depolarization (mV), 300 W/cm$^2$ |
|---|---|---|---|---|---|---|---|
| CheRiff | 2.0 ± 0.1 | 1.33 ± 0.08 | 4.5 ± 0.3 | 400 ± 40 | 16 ± 0.5 | 10.5 ± 2.8 | 2.3 ± 0.3 |
| ChIEF | 0.9 ± 0.1 | 0.81 ± 0.10 | 18 ± 1.8 | 51 ± 10 | 15 ± 2 | 15.0 ± 2.5 | 2.1 ± 0.15 |
| ChR2 H134R | 1.1 ± 0.1 | 0.65 ± 0.09 | 9.1 ± 0.7 | 40 ± 5 | 25 ± 4 | 2.2 ± 0.9 | 1.0 |

FIG. 5 shows application of CheRiff in cultured hippocampal neurons. FIG. 5A shows light micrographs (DIC) of *Scherffelia dubia* (strain CCAC 0053) in side view (top) and face view (bottom). Arrows mark eyespots (red). Strain and micrographs courtesy of CCAC [ccac.uni-koeln.de] and Sebastian Hess (Cologne Biocenter), respectively. FIG. 5B shows photomicrographic image of cultured rat hippocampal neuron expressing CheRiff-eGFP, imaged via eGFP fluorescence. FIG. 5C shows photocurrents induced by CheRiff and by Channelrhodopsin2 H134R with illumination at 488 nm, 500 mW/cm². FIG. 5D provides a graph showing comparison of photocurrents as a function of illumination intensity in matched cultures expressing CheRiff (n=5 cells) or ChR2 H134R (n=5 cells). Illumination was either over the whole cell or confined to the soma. FIG. 5E provides a graph showing spiking fidelity as a function of stimulation frequency and illumination intensity in neurons expressing CheRiff (n=5 cells).

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. An isolated light-activated ion channel polypeptide; wherein the light-activated ion channel polypeptide is activated when contacted with blue light; and the light-activated ion channel polypeptide comprises the amino acid sequence set forth as SEQ ID NO: 4, or a variant thereof comprising the amino acid sequence set forth as SEQ ID NO: 4 with one or more amino acid sequence modifications and with at least 90% amino acid identity to the corresponding sequence of SEQ ID NO: 4 with which it aligns.

2. The light-activated ion channel polypeptide of claim 1, wherein the polypeptide comprises the amino acid sequence of ChR86 (SEQ ID NO: 4).

3. The light-activated ion channel polypeptide of claim 1, wherein the variant polypeptide sequence comprises a D→A substitution at an amino acid residue corresponding to amino acid 124 of the amino acid sequence of ChR86 (SEQ ID NO: 4).

4. The light-activated ion channel polypeptide of claim 1, wherein the amino acid sequence of the light-activated ion channel polypeptide comprises the sequence set forth as SEQ ID NO: 8.

5. The light-activated ion channel polypeptide of claim 1, wherein the amino acid sequence of the light-activated ion channel polypeptide comprises the sequence set forth as SEQ ID NO: 4, with one or more amino acid sequence modifications and having at least 95% amino acid identity to the corresponding sequence set forth as SEQ ID NO: 4 with which it aligns.

6. The light-activated ion channel polypeptide of claim 1, wherein the amino acid sequence of the light-activated ion channel polypeptide has at least 98% amino acid identity to the corresponding sequence of SEQ ID NO: 4 with which it aligns.

7. The light-activated ion channel polypeptide of claim 1, wherein the amino acid sequence of the light-activated ion channel polypeptide has at least 99% amino acid identity to the corresponding sequence of SEQ ID NO: 4 with which it aligns.

8. A fusion protein comprising the light-activated ion channel polypeptide of claim 1.

9. A vector comprising a nucleic acid sequence encoding the light-activated ion channel polypeptide of claim 1.

10. A cell comprising the light-activated ion channel polypeptide of claim 1.

11. The cell of claim 10, wherein the cell is an excitable cell, and optionally wherein the cell is a mammalian cell.

12. A method of depolarizing a cell, the method comprising:
contacting a light-activated ion channel polypeptide expressed in a cell that is not a Chloromonas cell, with a blue light under conditions suitable to depolarize the cell and depolarizing the cell, wherein the light-activated ion channel polypeptide is activated when contacted by blue light and comprises an amino acid sequence set forth as SEQ ID NO: 4, or a variant thereof comprising the amino acid sequence set forth as SEQ ID NO: 4 with one or more amino acid sequence modifications and with at least 90% amino acid identity to the corresponding sequence of SEQ ID NO: 4 with which it aligns.

13. The method of claim 12, wherein the amino acid sequence of the light-activated ion channel polypeptide sequence comprises the sequence set forth as SEQ ID NO: 4 or SEQ ID NO: 8.

14. The method of claim 12, wherein the cell is a mammalian cell.

15. The method of claim 12, wherein the amino acid sequence of the light-activated ion channel polypeptide comprises the sequence set forth as SEQ ID NO: 4, with one or more amino acid sequence modifications and having at least 95% amino acid identity to the corresponding sequence set forth as SEQ ID NO: 4 with which it aligns.

16. The method of claim 12, wherein the amino acid sequence of the light-activated ion channel polypeptide comprises the sequence set forth as SEQ ID NO: 4, with one or more amino acid sequence modifications and having at least 98% amino acid identity to the corresponding sequence set forth as SEQ ID NO: 4 with which it aligns.

17. The method of claim 12, wherein the amino acid sequence of the light-activated ion channel polypeptide comprises the sequence set forth as SEQ ID NO: 4, with one or more amino acid sequence modifications and having at least 99% amino acid identity to the corresponding sequence set forth as SEQ ID NO: 4 with which it aligns.

18. A method of assessing the effect of a candidate compound on a cell, the method comprising,
a) contacting a light-activated ion channel polypeptide expressed in a test cell that is not a Chloromonas cell, with a blue light under conditions suitable for depolarization of the test cell; wherein the light-activated ion channel polypeptide is activated by blue light and comprises an amino acid sequence set forth as SEQ ID NO: 4, or a variant thereof comprising the amino acid sequence set forth as SEQ ID NO: 4 with one or more amino acid sequence modifications and with at least 90% amino acid identity to the corresponding sequence of SEQ ID NO: 4 with which it aligns;
b) contacting the test cell with a candidate compound; and
c) identifying the presence or absence of a change in depolarization or a change in a depolarization-mediated cell characteristic in the test cell contacted with the blue light and the candidate compound compared to depolarization or a depolarization-mediated cell characteristic, respectively, in a control cell contacted with the blue light and not contacted with the candidate compound; wherein a change in depolarization or a depolarization-mediated cell characteristic in the test cell compared to the control cell indicates an effect of the candidate compound on the test cell.

19. The method of claim 18, wherein the effect of the candidate compound is an effect on the depolarization of the test cell.

20. The method of claim 18, wherein the effect of the candidate compound is an effect on a depolarization-mediated cell characteristic in the test cell.

21. The method of claim 18, wherein the test cell is a mammalian cell.

22. The method of claim 18, wherein the amino acid sequence of the light-activated ion channel polypeptide comprises the sequence set forth as SEQ ID NO: 4, with one or more amino acid sequence modifications and having at least 95% amino acid identity to the corresponding sequence set forth as SEQ ID NO: 4 with which it aligns.

23. The method of claim 18, wherein the amino acid sequence of the light- activated ion channel polypeptide comprises the sequence set forth as SEQ ID NO: 4, with one or more amino acid sequence modifications and having at least 98% amino acid identity to the corresponding sequence set forth as SEQ ID NO: 4 with which it aligns.

24. The method of claim 18, wherein the amino acid sequence of the light-activated ion channel polypeptide comprises the sequence set forth as SEQ ID NO: 4, with one or more amino acid sequence modifications and having at least 99% amino acid identity to the corresponding sequence set forth as SEQ ID NO: 4 with which it aligns.

25. The method of claim 18, wherein, the amino acid sequence of the light-activated ion channel polypeptide comprises the sequence set forth as SEQ ID NO: 4 or SEQ ID NO: 8.

* * * * *